United States Patent
Zhan et al.

(10) Patent No.: US 12,258,607 B2
(45) Date of Patent: *Mar. 25, 2025

(54) METHODS FOR A CONTROLLED COENZYME $Q_{10}$ FERMENTATION PRODUCTION PROCESS

(71) Applicants: INNER MONGOLIA KINGDOMWAY PHARMACEUTICAL CO., LTD., Inner Mongolia (CN); XIAMEN KINGDOMWAY GROUP COMPANY, Fujian (CN)

(72) Inventors: Guanghuang Zhan, Xiamen (CN); Yi Wu, Xiamen (CN); Biqin Chen, Xiamen (CN); Zhichun Zhu, Xiamen (CN); Dan Li, Xiamen (CN)

(73) Assignees: INNER MONGOLIA KINGDOMWAY PHARMACEUTICAL CO., LTD., Hohhot (CN); XIAMEN KINGDOMWAY GROUP COMPANY, Xiamen (CN)

( * ) Notice: Subject to any disclaimer, the term of this patent is extended or adjusted under 35 U.S.C. 154(b) by 117 days.

This patent is subject to a terminal disclaimer.

(21) Appl. No.: 18/171,647

(22) Filed: Feb. 20, 2023

(65) Prior Publication Data
US 2023/0203543 A1 Jun. 29, 2023

Related U.S. Application Data

(63) Continuation of application No. 16/599,184, filed on Oct. 11, 2019, now Pat. No. 11,584,942, which is a continuation of application No. PCT/CN2019/085990, filed on May 8, 2019.

(51) Int. Cl.
*C12P 7/26* (2006.01)
*C12N 1/20* (2006.01)

(52) U.S. Cl.
CPC .................. *C12P 7/26* (2013.01); *C12N 1/20* (2013.01)

(58) Field of Classification Search
None
See application file for complete search history.

(56) References Cited

U.S. PATENT DOCUMENTS

| | | |
|---|---|---|
| 2013/0302862 A1 | 11/2013 | Wu et al. |
| 2013/0330789 A1 | 12/2013 | Chen et al. |
| 2018/0245113 A1 | 8/2018 | Yu et al. |
| 2021/0324391 A1 | 10/2021 | Yu et al. |

FOREIGN PATENT DOCUMENTS

| | | | |
|---|---|---|---|
| CN | 1986774 | A | 6/2007 |
| CN | 102399845 | A | 4/2012 |
| CN | 101519681 | B | 11/2012 |
| CN | 102876743 | A * | 1/2013 |
| CN | 103196860 | A | 7/2013 |
| CN | 103509729 | A | 1/2014 |
| CN | 104561154 | A | 4/2015 |
| CN | 102965272 | B | 11/2015 |
| WO | 2006113728 | A2 | 10/2006 |
| WO | 2008100782 | A2 | 8/2008 |

OTHER PUBLICATIONS

International Search Report in PCT/CN2019/085990 mailed on Feb. 6, 2020, 4 pages.
Written Opinion in PCT/CN2019/085990 mailed on Feb. 6, 2020, 5 pages.
Yen, Hongwei et al., Cultivation of Rhodobacter Sphaeroides in the Stirred Bioreactor with Different Feeding Strategies for CoQ10 Production, Applied Biochemistry and Biotechnology, 160: 1441-1449, 2010.
Nguyen Ba Kien et al., Coenzyme Q10 Production in a 150-1 Reactor by a Mutant Strain of Rhodobacter Sphaeroides, Journal of Industrial Microbiology & Biotechnology, 37: 521-529, 2010.
Alena Aliashkevich et al., New Insights Into the Mechanisms and Biological Roles of D-Amino Acids in Complex Eco-Systems, Frontiers in Microbiology, 9: 1-11, 2018.
Illana Kolodkin-Gal et al., D-Amino Acids Trigger Biofilm Disassembly, Science, 2010, 8 pages.
The Third Office Action in Chinese Application No. 201980003704.5 mailed on Apr. 13, 2024, 23 pages.
Zhao, Shoujing, Detection and Regulation of Biological Reaction Process, Jilin University Press, 2008, 11 pages.

* cited by examiner

*Primary Examiner* — Michelle F. Paguio Frising
(74) *Attorney, Agent, or Firm* — METIS IP LLC

(57) ABSTRACT

Controlled coenzyme $Q_{10}$ ($CoQ_{10}$) fermentation production processes and methods for controlling the $CoQ_{10}$ fermentation production processes are provided in the present disclosure. The processes may include growing a microbial culture of bacteria by providing a carbon source and an oxygen source for a predetermined period of time, thereby producing $CoQ_{10}$-containing bacteria, carbon dioxide, and lactate in the bacterial culture. During various stages of the production process, the concentration of carbon dioxide may be maintained at predetermined levels, respectively. Alternatively or additionally, during various stages of the production process, the concentration of lactate may be maintained at predetermined levels, respectively.

20 Claims, 7 Drawing Sheets bacter sphaeroides. The control of the fermentation production process is very important because a lack of comprehensive control may lead to fluctuations in the yield of $CoQ_{10}$ from batch to batch, as to both quantity and quality. Moreover, biofilms formed by the microbes may significantly affect the transfer efficiency of materials (e.g., oxygen, a carbon source) between the microbes and the fermentation medium. Therefore, it is desirable to provide more effective methods for controlling the $CoQ_{10}$ fermentation production process.

METHODS FOR A CONTROLLED COENZYME $Q_{10}$ FERMENTATION PRODUCTION PROCESS

CROSS-REFERENCE TO RELATED APPLICATIONS

This application is a continuation of U.S. patent application Ser. No. 16/599,184, filed on Oct. 11, 2019, which is a continuation of International Application No. PCT/CN2019/085990, filed on May 8, 2019, which designates the United States of America, the contents of which are incorporated herein by reference in their entirety.

TECHNICAL FIELD

The present disclosure generally relates to methods for a fermentation production process, and in particular, to methods for a controlled coenzyme $Q_{10}$ ($CoQ_{10}$) fermentation production process.

BACKGROUND $CoQ_{10}$ is a lipid-soluble quinone homolog. It is mainly present in mitochondria, lysosome, Golgi body, microsome, cell membrane and the like. $CoQ_{10}$ is a substance indispensable to the functional maintenance of the body. It is known to be involved in the activation of adenosine triphosphate (ATP) production as a constituent component of the electron transport system in mitochondria, antioxidant action in the body and membrane stabilization. Also, $CoQ_{10}$ is one of the important enzymes involved in the mitochondrial respiratory chain. $CoQ_{10}$ has been used in fields like food processing, pharmaceutics, cosmetics, or the like.

$CoQ_{10}$ may be produced through a fermentation production process using a microorganism strain, such as *Rhodobacter sphaeroides*. The control of the fermentation production process is very important because a lack of comprehensive control may lead to fluctuations in the yield of $CoQ_{10}$ from batch to batch, as to both quantity and quality. Moreover, biofilms formed by the microbes may significantly affect the transfer efficiency of materials (e.g., oxygen, a carbon source) between the microbes and the fermentation medium. Therefore, it is desirable to provide more effective methods for controlling the $CoQ_{10}$ fermentation production process.

SUMMARY

According to an aspect of the present disclosure, a controlled coenzyme $Q_{10}$ ($CoQ_{10}$) fermentation production process is provided. The process may include growing a microbial culture of bacteria by providing a carbon source and an oxygen source for a predetermined period of time, thereby producing $CoQ_{10}$-containing bacteria and carbon dioxide ($CO_2$) in the microbial culture, wherein: (1) during 0-16 h of growing the microbial culture, a concentration of carbon dioxide in an exhaust gas of the microbial culture may be maintained at 0.5%-13%; (2) during 16-48 h of growing the microbial culture, the concentration of carbon dioxide may be maintained at 3%-15%; (3) during 48-80 h of growing the microbial culture, the concentration of carbon dioxide may be maintained at 3%-12%; and (4) after 80 h of growing the microbial culture, the concentration of carbon dioxide may be maintained at 2%-10%.

In some embodiments, during 0-16 h of growing the microbial culture, the concentration of carbon dioxide may be maintained at 1%-10%.

In some embodiments, during 0-8 h of growing the microbial culture, the concentration of carbon dioxide may be maintained at 1%-5%.

In some embodiments, during 8-16 h of growing the microbial culture, the concentration of carbon dioxide may be maintained at 3%-10%.

In some embodiments, during 16-48 h of growing the microbial culture, the concentration of carbon dioxide may be maintained at 5%-13%.

In some embodiments, during 16-32 h of growing the microbial culture, the concentration of carbon dioxide may be maintained at 5%-13%.

In some embodiments, during 32-48 h of growing the microbial culture, the concentration of carbon dioxide may be maintained at 6%-11%.

In some embodiments, during 48-80 h of growing the microbial culture, the concentration of carbon dioxide may be maintained at 4%-10%.

In some embodiments, during 48-64 h of growing the microbial culture, the concentration of carbon dioxide may be maintained at 5%-10%.

In some embodiments, during 64-80 h of growing the microbial culture, the concentration of carbon dioxide may be maintained at 4%-9%.

In some embodiments, after 80 h of growing the microbial culture, the concentration of carbon dioxide may be further maintained at 3%-8%.

According to another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 0-8 h of growing the microbial culture, a concentration of carbon dioxide in an exhaust gas of the microbial culture may be maintained at 1%-5%.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 8-16 h of growing the microbial culture, a concentration of carbon dioxide in an exhaust gas of the microbial culture may be maintained at 3%-10%.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 16-32 h of growing the microbial culture, a concentration of carbon dioxide in an exhaust gas of the microbial culture may be maintained at 5%-13%.

According to yet another aspect of the present disclosure, a controlled $CoQ_{10}$ fermentation production process, comprising growing a microbial culture of *Rhodobacter sphaeroides* by providing a carbon source and an oxygen source for a predetermined period of time, thereby producing $CoQ_{10}$-containing bacteria and carbon dioxide in the microbial culture. During 32-48 h of growing the microbial culture, a concentration of carbon dioxide in an exhaust gas of the microbial culture may be maintained at 6%-11%.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 48-64 h of growing the microbial culture, a concentration of carbon dioxide in an exhaust gas of the microbial culture may be maintained at 5%-10%.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 64-80 h of growing the microbial culture, a concentration of carbon dioxide in an exhaust gas of the microbial culture may be maintained at 4%-9%.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. After 80 h of growing the microbial culture, a concentration of carbon dioxide in an exhaust gas of the microbial culture may be further maintained at 3%-8%.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture, wherein: (1) during 0-16 h of growing the microbial culture, a concentration of carbon dioxide in an exhaust gas of the microbial culture may be maintained at 1%-10%; (2) during 16-48 h of growing the microbial culture, the concentration of carbon dioxide may be maintained at 5%-13%; (3) during 48-80 h of growing the microbial culture, the concentration of carbon dioxide may be maintained at 4%-10%; and (4) during 80-100 h of growing the microbial culture, the concentration of carbon dioxide may be maintained at 3%-8%.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture, wherein: (1) during 0-8 h of growing the microbial culture, a concentration of carbon dioxide in an exhaust gas of the microbial culture may be maintained at 1%-5%; (2) during 8-16 h of growing the microbial culture, the concentration of carbon dioxide may be maintained at 3%-10%; (3) during 16-32 h of growing the microbial culture, the concentration of carbon dioxide may be maintained at 5%-13%; (4) during 32-48 h of growing the microbial culture, the concentration of carbon dioxide may be maintained at 6%-11%; (5) during 48-64 h of growing the microbial culture, the concentration of carbon dioxide may be maintained at 5%-10%; (6) during 64-80 h of growing the microbial culture, the concentration of carbon dioxide may be maintained at 4%-9%; and (7) after 80 h of growing the microbial culture, the concentration of carbon dioxide may be further maintained at 3%-8%.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and carbon dioxide in the microbial culture. During 0-8 h of growing the microbial culture, a concentration of carbon dioxide in an exhaust gas of the microbial culture may be maintained at 1%-5%; and during a remaining time period of growing the microbial culture, the concentration of carbon dioxide may be maintained at 3%-13%.

In some embodiments, during 8-16 h of growing the microbial culture, the concentration of carbon dioxide may be maintained at 3%-10%; and during a remaining time period of growing the microbial culture, the concentration of carbon dioxide may be maintained at 3%-13%.

In some embodiments, during 16-32 h of growing the microbial culture, the concentration of carbon dioxide may be maintained at 5%-13%; and during a remaining time period of growing the microbial culture, the concentration of carbon dioxide may be maintained at 3%-11%.

In some embodiments, during 32-48 h of growing the microbial culture, the concentration of carbon dioxide may be maintained at 6%-11%; and during a remaining time period of growing the microbial culture, the concentration of carbon dioxide may be maintained at 3%-10%.

In some embodiments, during 48-64 h of growing the microbial culture, the concentration of carbon dioxide may be maintained at 5%-10%; and during a remaining time period of growing the microbial culture, the concentration of carbon dioxide may be maintained at 3%-9%.

In some embodiments, during 64-80 h of growing the microbial culture, the concentration of carbon dioxide may be maintained at 4%-9%; and during a remaining time period of growing the microbial culture, the concentration of carbon dioxide may be maintained at 3%-8%.

In some embodiments, the concentration of carbon dioxide may be maintained by increasing or decreasing rotor speed, tank pressure, or air supply rate.

In some embodiments, the microbial culture may be growing in a tank with a volume capacity of 0.5 L-2000 $m^3$.

In some embodiments, the microbial culture may be growing in a tank with a volume capacity of 100 L, 160 $m^3$, 325 $m^3$, or 500 $m^3$.

According to still another aspect of the present disclosure, a controlled coenzyme $Q_{10}$ fermentation production process is provided. The process may include growing a microbial culture of bacteria by providing a carbon source and an oxygen source for a predetermined period of time, thereby producing $CoQ_{10}$-containing bacteria and lactate in the microbial culture, wherein: (1) during 0-16 h of growing the microbial culture, the concentration of lactate in the microbial culture may be maintained at 5-75 mg/L; (2) during 16-48 h of growing the microbial culture, the concentration of lactate in the microbial culture may be maintained at 10-120 mg/L; (3) during 48-80 h of growing the microbial culture, the concentration of lactate in the microbial culture may be maintained at 20-180 mg/L; and (4) after 80 h of growing the microbial culture, the concentration of lactate in the microbial culture may be maintained at 40-120 mg/L.

In some embodiments, during 0-16 h of growing the microbial culture, the concentration of lactate in the microbial culture may be further maintained at 10-50 mg/L.

In some embodiments, during 0-8 h of growing the microbial culture, the concentration of lactate in the microbial culture may be maintained at 10-30 mg/L.

In some embodiments, during 8-16 h of growing the microbial culture, the concentration of lactate in the microbial culture may be maintained at 10-50 mg/L.

In some embodiments, during 16-48 h of growing the microbial culture, the concentration of lactate in the microbial culture may be further maintained at 20-100 mg/L.

In some embodiments, during 16-32 h of growing the microbial culture, the concentration of lactate in the microbial culture may be maintained at 20-50 mg/L.

In some embodiments, during 32-48 h of growing the microbial culture, the concentration of lactate in the microbial culture may be maintained at 30-100 mg/L.

In some embodiments, during 48-80 h of growing the microbial culture, the concentration of lactate in the microbial culture may be further maintained at 30-150 mg/L.

In some embodiments, during 48-64 h of growing the microbial culture, the concentration of lactate in the microbial culture may be maintained at 30-150 mg/L.

In some embodiments, during 64-80 h of growing the microbial culture, the concentration of lactate in the microbial culture may be maintained at 50-150 mg/L.

In some embodiments, after 80 h of growing the microbial culture, the concentration of lactate in the microbial culture may be further maintained at 50-100 mg/L.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 0-8 h of growing the microbial culture, the concentration of lactate in the microbial culture may be maintained at 10-30 mg/L.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 8-16 h of growing the microbial culture, the concentration of lactate in the microbial culture may be maintained at 10-50 mg/L.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 16-32 h of growing the microbial culture, the concentration of lactate in the microbial culture may be maintained at 20-50 mg/L.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 32-48 h of growing the microbial culture, the concentration of lactate in the microbial culture may be maintained at 30-100 mg/L.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 48-64 h of growing the microbial culture, the concentration of lactate in the microbial culture may be maintained at 30-150 mg/L.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 64-80 h of growing the microbial culture, the concentration of lactate in the microbial culture may be maintained at 50-150 mg/L.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. After 80 h of growing the microbial culture, the concentration of lactate in the microbial culture may be further maintained at 50-100 mg/L.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture, wherein: (1) during 0-16 h of growing the microbial culture, the concentration of lactate in the microbial culture may be maintained at 10-50 mg/L; (2) during 16-48 h of growing the microbial culture, the concentration of lactate in the microbial culture may be maintained at 20-100 mg/L; (3) during 48-80 h of growing the microbial culture, the concentration of lactate in the microbial culture may be maintained at 30-150 mg/L; and (4) after 80 h of growing the microbial culture, the concentration of lactate in the microbial culture may be maintained at 50-100 mg/L.

According to yet another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture, wherein: (1) during 0-8 h of growing the microbial culture, the concentration of lactate in the microbial culture may be maintained at 10-30 mg/L; (2) during 8-16 h of growing the microbial culture, the concentration of lactate in the microbial culture may be maintained at 10-50 mg/L; (3) during 16-32 h of growing the microbial culture, the concentration of lactate in the microbial culture may be maintained at 20-50 mg/L; (4) during 32-48 h of growing the microbial culture, the concentration of lactate in the microbial culture may be maintained at 30-100 mg/L; (5) during 48-64 h of growing the microbial culture, the concentration of lactate in the microbial culture may be maintained at 30-150 mg/L; (6) during 64-80 h of growing the microbial culture, the concentration of lactate in the microbial culture may be maintained at 50-150 mg/L; and (7) after 80 h of growing the microbial culture, the concentration of lactate in the microbial culture may be further maintained at 50-100 mg/L.

According to still another aspect of the present disclosure, a controlled $CoQ_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria and lactate in the microbial culture. During 0-8 h of growing the microbial culture, the concentration of lactate in the microbial culture may be maintained at 10-30 mg/L; and during a remaining time period of growing the microbial culture, the concentration of lactate in the microbial culture may be maintained at 10-150 mg/L.

In some embodiments, during 8-16 h of growing the microbial culture, the concentration of lactate in the microbial culture may be maintained at 10-50 mg/L; and during a remaining time period of growing the microbial culture, the concentration of lactate in the microbial culture may be maintained at 20-150 mg/L.

In some embodiments, during 16-32 h of growing the microbial culture, the concentration of lactate in the microbial culture may be maintained at 20-50 mg/L; and during a remaining time period of growing the microbial culture, the concentration of lactate in the microbial culture may be maintained at 30-150 mg/L.

In some embodiments, during 32-48 h of growing the microbial culture, the concentration of lactate in the microbial culture may be maintained at 30-100 mg/L; and during a remaining time period of growing the microbial culture, the concentration of lactate in the microbial culture may be maintained at 30-150 mg/L.

In some embodiments, during 48-64 h of growing the microbial culture, the concentration of lactate in the microbial culture may be maintained at 30-150 mg/L; and during a remaining time period of growing the microbial culture, the concentration of lactate in the microbial culture may be maintained at 50-150 mg/L.

In some embodiments, during 64-80 h of growing the microbial culture, the concentration of lactate in the microbial culture may be maintained at 50-150 mg/L; and during a remaining time period of growing the microbial culture, the concentration of lactate in the microbial culture may be maintained at 50-100 mg/L.

In some embodiments, the concentration of lactate in the microbial culture may be maintained by increasing or decreasing rotor speed, tank pressure, or air supply rate.

In some embodiments, the microbial culture may be growing in a tank with a volume capacity of 0.5 L-2000 $m^3$.

In some embodiments, the microbial culture may be growing in a tank with a volume capacity of 100 L, 160 $m^3$, 325 $m^3$, or 500 $m^3$.

According to yet another aspect of the present disclosure, a controlled coenzyme $Q_{10}$ fermentation production process is provided. The process may include growing a microbial culture of bacteria by providing a carbon source and an oxygen source for a predetermined period of time, thereby producing $CoQ_{10}$-containing bacteria, carbon dioxide, and lactate in the microbial culture, wherein: (1) during 0-16 h of growing the microbial culture, a concentration of carbon dioxide in an exhaust gas of the microbial culture may be maintained at 1%-10%, and the concentration of lactate in the microbial culture may be maintained at 10-50 mg/L; (2) during 16-48 h of growing the microbial culture, the concentration of carbon dioxide may be maintained at 3%-15%, and the concentration of lactate in the microbial culture may be maintained at 20-100 mg/L; (3) during 48-80 h of growing the microbial culture, the concentration of carbon dioxide may be maintained at 3%-12%, and the concentration of lactate in the microbial culture may be maintained at 30-150 mg/L; and (4) after 80 h of growing the microbial culture, the concentration of carbon dioxide may be maintained at 2%-10%, and the concentration of lactate in the microbial culture may be maintained at 50-100 mg/L.

In some embodiments, during 0-8 h of growing the microbial culture, the concentration of carbon dioxide may be maintained at 1%-5%, and the concentration of lactate in the microbial culture may be maintained at 10-30 mg/L.

In some embodiments, during 8-16 h of growing the microbial culture, the concentration of carbon dioxide may be maintained at 3%-10%, and the concentration of lactate in the microbial culture may be maintained at 10-50 mg/L.

In some embodiments, during 16-32 h of growing the microbial culture, the concentration of carbon dioxide may be maintained at 5%-13%, and the concentration of lactate in the microbial culture may be maintained at 20-50 mg/L.

In some embodiments, during 32-48 h of growing the microbial culture, the concentration of carbon dioxide may be maintained at 6%-11%, and the concentration of lactate in the microbial culture may be maintained at 30-100 mg/L.

In some embodiments, during 48-64 h of growing the microbial culture, the concentration of carbon dioxide may be maintained at 5%-10%, and the concentration of lactate in the microbial culture may be maintained at 30-150 mg/L.

In some embodiments, during 64-80 h of growing the microbial culture, the concentration of carbon dioxide may be maintained at 4%-9%, and the concentration of lactate in the microbial culture may be maintained at 50-150 mg/L.

According to still another aspect of the present disclosure, a controlled coenzyme $Q_{10}$ fermentation production process is provided. The process may include growing a microbial culture of *Rhodobacter sphaeroides* by providing a carbon source and an oxygen source for a predetermined period of time, thereby producing $CoQ_{10}$-containing bacteria, carbon dioxide, and lactate in the microbial culture, wherein: (1) during 0-8 h of growing the microbial culture, a concentration of carbon dioxide in an exhaust gas of the microbial culture may be maintained at 1%-10%, and the concentration of lactate in the microbial culture may be maintained at 10-50 mg/L; (2) during 8-16 h of growing the microbial culture, the concentration of carbon dioxide may be maintained at 1%-10%, and the concentration of lactate in the microbial culture may be maintained at 10-50 mg/L; (3) during 16-32 h of growing the microbial culture, the concentration of carbon dioxide may be maintained at 3%-15%, and the concentration of lactate in the microbial culture may be maintained at 20-100 mg/L; (4) during 32-48 h of growing the microbial culture, the concentration of carbon dioxide may be maintained at 3%-15%, and the concentration of lactate in the microbial culture may be maintained at 20-100 mg/L; (5) during 48-64 h of growing the microbial culture, the concentration of carbon dioxide may be maintained at 3%-12%, and the concentration of lactate in the microbial culture may be maintained at 30-150 mg/L; (6) during 64-80 h of growing the microbial culture, the concentration of carbon dioxide may be maintained at 3%-12%, and the concentration of lactate in the microbial culture may be maintained at 30-150 mg/L; and (7) after 80 h of growing the microbial culture, the concentration of carbon dioxide may be maintained at 2%-10%, and the concentration of lactate in the microbial culture may be maintained at 50-100 mg/L.

In some embodiments, the concentration of the carbon dioxide and the concentration of lactate in the microbial culture may be maintained by increasing or decreasing rotor speed, tank pressure, or air supply rate.

According to yet another aspect of the present disclosure, a coenzyme $Q_{10}$ fermentation production process is provided. The process may include growing a microbial culture of bacteria in a first tank by providing a carbon source and an oxygen source, monitoring a first fermentation parameter of the microbial culture in the first tank, and determining whether the first fermentation parameter of the microbial culture in the first tank satisfies a first condition. The process may further include, in response to a determination that the first fermentation parameter does not satisfy the first condition, moving a portion of the microbial culture in the first tank into a second tank. The process may further include continuing to grow the microbial cultures in both the first tank and the second tank.

In some embodiments, the first fermentation parameter may be a concentration of carbon dioxide. The first condition may include (1) during 0-16 h of growing the microbial culture, a concentration of carbon dioxide in an exhaust gas of the microbial culture may be maintained at 1%-10%; (2) during 16-48 h of growing the microbial culture, the concentration of carbon dioxide may be maintained at 5%-13%; (3) during 48-80 h of growing the microbial culture, the concentration of carbon dioxide may be maintained at 4%-10%; and (4) after 80 h of growing the microbial culture, the concentration of carbon dioxide may be maintained at 3%-8%.

In some embodiments, the first fermentation parameter may be a concentration of carbon dioxide. The first condition includes: (1) during 0-8 h of growing the microbial culture, the concentration of carbon dioxide may be maintained at 1%-5%; (2) during 8-16 h of growing the microbial culture, the concentration of carbon dioxide may be maintained at 3%-10%; (3) during 16-32 h of growing the microbial culture, the concentration of carbon dioxide may be maintained at 5%-13%; (4) during 32-48 h of growing the microbial culture, the concentration of carbon dioxide may be maintained at 6%-11%; (5) during 48-64 h of growing the microbial culture, the concentration of carbon dioxide may be maintained at 5%-10%; (6) during 64-80 h of growing the microbial culture, the concentration of carbon dioxide may be maintained at 4%-9%; and (7) after 80 h of growing the microbial culture, the concentration of carbon dioxide may be further maintained at 3%-8%.

In some embodiments, the first fermentation parameter may be a concentration of carbon dioxide. The first condition may include during 16-48 h of growing the microbial culture, the concentration of carbon dioxide may be maintained at 5%-13%.

In some embodiments, the first fermentation parameter may be a concentration of carbon dioxide. The first condition may include that during 48-80 h of growing the microbial culture, the concentration of carbon dioxide may be maintained at 4%-10%.

In some embodiments, the first fermentation parameter may be a concentration of lactate. The first condition may include: (1) during 0-16 h of growing the microbial culture, the concentration of lactate may be maintained at 10-50 mg/L; (2) during 16-48 h of growing the microbial culture, the concentration of lactate may be maintained at 20-100 mg/L; (3) during 48-80 h of growing the microbial culture, the concentration of lactate may be maintained at 30-150 mg/L; and (4) after 80 h of growing the microbial culture, the concentration of lactate may be maintained at 50-100 mg/L.

In some embodiments, the first fermentation parameter may be a concentration of lactate. The first condition may include (1) during 0-8 h of growing the microbial culture, the concentration of lactate in the microbial culture may be maintained at 10-30 mg/L; (2) during 8-16 h of growing the microbial culture, the concentration of lactate in the microbial culture may be maintained at 10-50 mg/L; (3) during 16-32 h of growing the microbial culture, the concentration of lactate in the microbial culture may be maintained at 20-50 mg/L; (4) during 32-48 h of growing the microbial culture, the concentration of lactate in the microbial culture may be maintained at 30-100 mg/L; (5) during 48-64 h of growing the microbial culture, the concentration of lactate in the microbial culture may be maintained at 30-150 mg/L; (6) during 64-80 h of growing the microbial culture, the concentration of lactate in the microbial culture may be maintained at 50-150 mg/L; and (7) after 80 h of growing the microbial culture, the concentration of lactate in the microbial culture may be further maintained at 50-100 mg/L.

In some embodiments, the first fermentation parameter may be a concentration of lactate. The first condition may include that during 16-48 h of growing the microbial culture, the concentration of lactate in the microbial culture may be maintained at 20-100 mg/L.

In some embodiments, the first fermentation parameter may be a concentration of lactate. The first condition may include during 48-80 h of growing the microbial culture, the concentration of lactate in the microbial culture may be maintained at 30-150 mg/L.

According to yet another aspect of the present disclosure, a coenzyme $Q_{10}$ fermentation production process is provided. The process may include growing a microbial culture of *Rhodobacter sphaeroides* in a first tank by providing a carbon source and an oxygen source, monitoring a first fermentation parameter and a second fermentation parameter of the microbial culture in the first tank and determining whether the first fermentation parameter of the microbial culture in the first tank satisfies a first condition and whether the second fermentation parameter of the microbial culture in the first tank satisfies a second condition. The process may further include, in response to a determination that the first fermentation parameter does not satisfy the first condition and that the second first fermentation parameter does not satisfy the first condition, moving a portion of the microbial culture in the first tank into a second tank. The process may further include continuing to grow the microbial cultures in both the first tank and the second tank.

In some embodiments, the first fermentation parameter may be a concentration of carbon dioxide in an exhaust gas of the microbial culture, and the second fermentation parameter may be a concentration of lactate. The first condition may include that during 16-48 h of growing the microbial culture, the concentration of carbon dioxide may be maintained at 5%-13%. The second condition may include that during 16-48 h of growing the microbial culture, the concentration of lactate in the microbial culture may be maintained at 20-100 mg/L.

In some embodiments, the first fermentation parameter may be a concentration of carbon dioxide in an exhaust gas of the microbial culture, and the second fermentation parameter may be a concentration of lactate, the first condition may include that during 48-80 h of growing the microbial culture, the concentration of carbon dioxide may be maintained at 4%-10%. The second condition may include that during 48-80 h of growing the microbial culture, the concentration of lactate in the microbial culture may be maintained at 30-150 mg/L.

According to still another aspect of the present disclosure, a coenzyme $Q_{10}$ fermentation production process is provided. The process may include growing a microbial culture of *Rhodobacter sphaeroides* in a first tank by providing a carbon source and an oxygen source, monitoring a first fermentation parameter of the microbial culture in the first tank, and determining whether the first fermentation parameter of the microbial culture in the first tank satisfies a first condition. The process may further include, in response to a determination that the first fermentation parameter does not satisfy the first condition, moving a portion of the microbial culture in the first tank into another tank, continuing to grow the microbial cultures in all the tanks, until an overall culturing time reaches a pre-determined time threshold.

In some embodiments, the first fermentation parameter may be a concentration of carbon dioxide in an exhaust gas of the microbial culture. The first condition may include during 16-48 h of growing the microbial culture, the concentration of carbon dioxide may be maintained at 5%-13%.

In some embodiments, the first fermentation parameter may be a concentration of carbon dioxide in an exhaust gas of the microbial culture. The first condition may include during 48-80 h of growing the microbial culture, the concentration of carbon dioxide may be maintained at 4%-10%.

In some embodiments, the first fermentation parameter may be a concentration of lactate, and the first condition may include that during 16-48 h of growing the microbial culture, the concentration of lactate in the microbial culture may be maintained at 20-100 mg/L.

In some embodiments, the first fermentation parameter may be a concentration of lactate. The first condition may include that during 48-80 h of growing the microbial culture, the concentration of lactate in the microbial culture may be maintained at 30-150 mg/L.

In some embodiments, the predetermined time threshold may be determined based on autolysis of the *Rhodobacter sphaeroides*.

In some embodiments, the concentration of the carbon dioxide and the concentration of lactate in the microbial culture may be maintained by increasing or decreasing rotor speed, tank pressure, or air supply rate.

In some embodiments, a portion of the microbial culture may be 5%-60% of the microbial culture in the first tank.

In some embodiments, a portion of the microbial culture may be 10%-50% of the microbial culture in the first tank.

In some embodiments, a portion of the microbial culture may be 25%-50% of the microbial culture in the first tank.

In some embodiments, a portion of the microbial culture may be 50% of the microbial culture in the first tank.

According to still another aspect of the present disclosure, a method of inhibiting formation of biofilm during coenzyme $Q_{10}$ fermentation production process is provided. The method may include growing a microbial culture of bacteria by providing a carbon source and an oxygen source, monitoring one or more fermentation parameters of the microbial culture, and determining whether the one or more fermentation parameters of the microbial culture satisfy a set of parameter conditions. The method may further include, in response to a determination that the one or more fermentation parameters satisfy the set of parameter conditions, adding D-amino acid to the microbial culture to a predetermined concentration.

In some embodiments, the D-amino acid may include one or more of D-tyrosine, D-aspartic acid, D-arginine, D-methionine, D-leucine, D-tryptophan, and D-phenylalanine.

In some embodiments, the predetermined concentration of the D-amino acid may be 1 μM-5 mM.

In some embodiments, a concentration of the D-amino acid may be 10 μM-2 mM.

In some embodiments, a concentration of the D-amino acid may be 100 μM-1 mM.

In some embodiments, the one or more parameters include a concentration of carbon dioxide in the microbial culture; and the set of parameter conditions include that a concentration of carbon dioxide in an exhaust gas of the microbial culture may be less than 3%.

In some embodiments, the one or more parameters include a concentration of carbon dioxide in an exhaust gas of the microbial culture; and the set of parameter conditions include that the concentration of carbon dioxide may be less than 3% during 16-48 h of growing the microbial culture.

In some embodiments, the one or more parameters may include a concentration of carbon dioxide in an exhaust gas of the microbial culture. The set of parameter conditions may include that the concentration of carbon dioxide may be less than 3% during 48-80 h of growing the microbial culture.

In some embodiments, the one or more parameters may include a concentration of carbon dioxide in an exhaust gas of the microbial culture. The set of parameter conditions may include that the concentration of carbon dioxide may be less than 2% after 80 h of growing the microbial culture.

In some embodiments, the one or more parameters may include a concentration of lactate in the microbial culture, and the set of parameter conditions may include that the concentration of lactate in the microbial culture may be more than 50 mg/L.

In some embodiments, the one or more parameters may include a concentration of lactate in the microbial culture, and the set of parameter conditions may include that the concentration of lactate in the microbial culture may be more than 120 mg/L during 16-48 h of growing the microbial culture.

In some embodiments, the one or more parameters may include a concentration of lactate in the microbial culture, and the set of parameter conditions may include that the concentration of lactate in the microbial culture may be more than 180 mg/L during 48-80 h of growing the microbial culture.

In some embodiments, the one or more parameters may include a concentration of lactate in the microbial culture, and the set of parameter conditions may include that the concentration of lactate in the microbial culture may be more than 120 mg/L after 80 h of growing the microbial culture.

In some embodiments, the one or more parameters may include a concentration of carbon dioxide in an exhaust gas of the microbial culture and a concentration of lactate in the microbial culture, and the set of parameter conditions may include that the concentration of carbon dioxide may be less than 3% and the concentration of lactate in the microbial culture may be more than 50 mg/L.

In some embodiments, the D-amino acid may be in the form of a mixture, including D-tyrosine, D-aspartic acid, D-arginine, and D-methionine.

In some embodiments, the mixture may include 30-50% D-tyrosine by weight, 10-20% D-aspartic acid by weight, about 30% D-arginine by weight, and about 15% D-methionine weight.

According to yet another aspect of the present disclosure, a controlled fermentation production process that is optimized for producing $CoQ_{10}$ is provided. The process may include growing a microbial culture for a predetermined period of time in a medium in a tank that may be being stirred by stirrers connected to rotors, thereby producing $CoQ_{10}$-containing bacteria. For optimized results, the process may further include: (1) during 0-16 h time period of growing the microbial culture, maintaining a rotor speed of the rotors between 50-150 rpm for more than 80% of the 0-16 h time period to keep a concentration of carbon dioxide in an exhaust gas of the microbial culture at 1%-10%; (2) during 16-48 h time period of growing the microbial culture, maintaining the rotor speed between 50-150 rpm for more than 80% of the 16-48 h time period to keep the concentration of carbon dioxide at 5%-13%; (3) during 48-80 h time period of growing the microbial culture, maintaining the rotor speed between 50-150 rpm for more than 80% of the 48-80 h time period to keep the concentration of carbon dioxide at 4%-10%; and (4) during a time period after 80 h of growing the microbial culture, maintaining the rotor speed between 50-150 rpm for more than 80% of the time period after 80 h to keep the concentration of carbon dioxide at 3%-8%.

According to still another aspect of the present disclosure, a controlled fermentation production process optimized for producing $CoQ_{10}$ is provided. The process may include growing a microbial culture for a predetermined period of time in a medium in a tank, thereby producing $CoQ_{10}$-containing bacteria, wherein for optimized results. The process may further include: (1) during 0-16 h time period of growing the microbial culture, maintaining a tank pressure between 0.02-0.08 MPa for more than 80% of the 0-16 h time period to keep a concentration of carbon dioxide in an exhaust gas of the microbial culture at 1%-10%; (2) during 16-48 h time period of growing the microbial culture, maintaining the tank pressure between 0.02-0.08 MPa for more than 80% of the 16-48 h time period to keep the concentration of carbon dioxide at 5%-13%; (3) during 48-80 h time period of growing the microbial culture, maintaining the tank pressure between 0.02-0.08 MPa for more than 80% of the 48-80 h time period to keep the concentration of carbon dioxide at 4%-10%; and (4) during a time period after 80 h of growing the microbial culture, maintaining the tank pressure between 0.02-0.08 MPa for more than 80% of the time period after 80 h to keep the concentration of carbon dioxide at 3%-8%.

According to yet another aspect of the present disclosure, a controlled fermentation production process, optimized for producing $CoQ_{10}$ is provided. The process may include growing a microbial culture for a predetermined period of time in a medium in a tank and providing an air supply that includes a carbon source, thereby producing $CoQ_{10}$-containing bacteria. For optimized results, the process may further include: (1) during 0-16 h time period of growing the microbial culture, maintaining an air supply rate between 0.2-1.0 air volume/culture volume per minute (VVM) for more than 80% of the 0-16 h time period to keep a concentration of carbon dioxide in an exhaust gas of the microbial culture at 1%-10%; (2) during 16-48 h time period of growing the microbial culture, maintaining the air supply rate between 0.2-1.0 VVM for more than 80% of the 16-48 h time period to keep the concentration of carbon dioxide at 5%-13%; (3) during 48-80 h time period of growing the microbial culture, maintaining the air supply rate between 0.2-1.0 VVM for more than 80% of the 48-80 h time period to keep the concentration of carbon dioxide at 4%-10%; and (4) during a time period after 80 h of growing the microbial culture, maintaining the air supply rate between 0.2-1.0 VVM for more than 80% of the time period after 80 h to keep the concentration of carbon dioxide at 3%-8%.

According to still another aspect of the present disclosure, a controlled fermentation production process optimized for producing $CoQ_{10}$ is provided. The process may include growing a microbial culture for a predetermined period of time in a medium that may be being stirred by stirrers connected to rotors, thereby producing $CoQ_{10}$-containing bacteria. For optimized results, the process may further include: (1) during 0-16 h time period of growing the microbial culture, maintaining a rotor speed of the rotors between 50-150 rpm for more than 80% of the 0-16 h time period to keep a concentration of lactate in the microbial culture at 10-50 mg/L; (2) during 16-48 h time period of growing the microbial culture, maintaining the rotor speed between 50-150 rpm for more than 80% of the 16-48 h time period to keep the concentration of lactate in the microbial culture at 20-100 mg/L; (3) during 48-80 h time period of growing the microbial culture, maintaining the rotor speed between 50-150 rpm for more than 80% of the 48-80 h time period to keep the concentration of lactate in the microbial culture at 30-150 mg/L; and (4) during a time period after 80 h of growing the microbial culture, maintaining rotor speed between 50-150 rpm for more than 80% of the time period after 80 h to keep the concentration of lactate in the microbial culture at 50-100 mg/L.

According to yet another aspect of the present disclosure, a controlled fermentation production process optimized for producing $CoQ_{10}$ is provided. The process may include growing a microbial culture for a predetermined period of time in a medium in a tank, thereby producing $CoQ_{10}$-containing bacteria, wherein for optimized results, the process may further include: (1) during 0-16 h time period of growing the microbial culture, maintaining a tank pressure between 0.02-0.08 MPa for more than 80% of the 0-16 h time period to keep a concentration of lactate in the microbial culture at 10-50 mg/L; (2) during 16-48 h time period of growing the microbial culture, maintaining the tank pressure between 0.02-0.08 MPa for more than 80% of the 16-48 h time period to keep the concentration of lactate in the microbial culture at 20-100 mg/L; (3) during 48-80 h time period of growing the microbial culture, maintaining the tank pressure between 0.02-0.08 MPa for more than 80% of the 48-80 h time period to keep the concentration of lactate in the microbial culture at 30-150 mg/L; and (4) during a time period after 80 h of growing the microbial culture, maintaining the tank pressure between 0.02-0.08 MPa for more than 80% of the time period after 80 h to keep the concentration of lactate in the microbial culture at 50-100 mg/L.

According to yet another aspect of the present disclosure, a controlled fermentation production process optimized for producing $CoQ_{10}$ is provided. The process may include growing a microbial culture for a predetermined period of time in a medium in a tank and providing an air supply that includes a carbon source, thereby producing $CoQ_{10}$-containing bacteria. For optimized results, the process may further include: (1) during 0-16 h time period of growing the microbial culture, maintaining an air supply rate between 0.2-1.0 VVM for more than 80% of the 0-16 h time period to keep a concentration of lactate in the microbial culture at 10-50 mg/L; (2) during 16-48 h time period of growing the microbial culture, maintaining the air supply rate between 0.2-1.0 VVM for more than 80% of the 16-48 h time period to keep the concentration of lactate in the microbial culture at 20-100 mg/L; (3) during 48-80 h time period of growing the microbial culture, maintaining the air supply rate between 0.2-1.0 VVM for more than 80% of the 48-80 h time period to keep the concentration of lactate in the microbial culture at 30-150 mg/L; and (4) during a time period after 80 h of growing the microbial culture, maintaining the air supply rate between 0.2-1.0 VVM for more than 80% of the time period after 80 h to keep the concentration of lactate in the microbial culture at 50-100 mg/L.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. It should be noted that the drawings are not to scale. These embodiments are non-limiting exemplary embodiments, in which like reference numerals represent similar structures throughout the several views of the drawings, and wherein.

DETAILED DESCRIPTION

Figure 1:
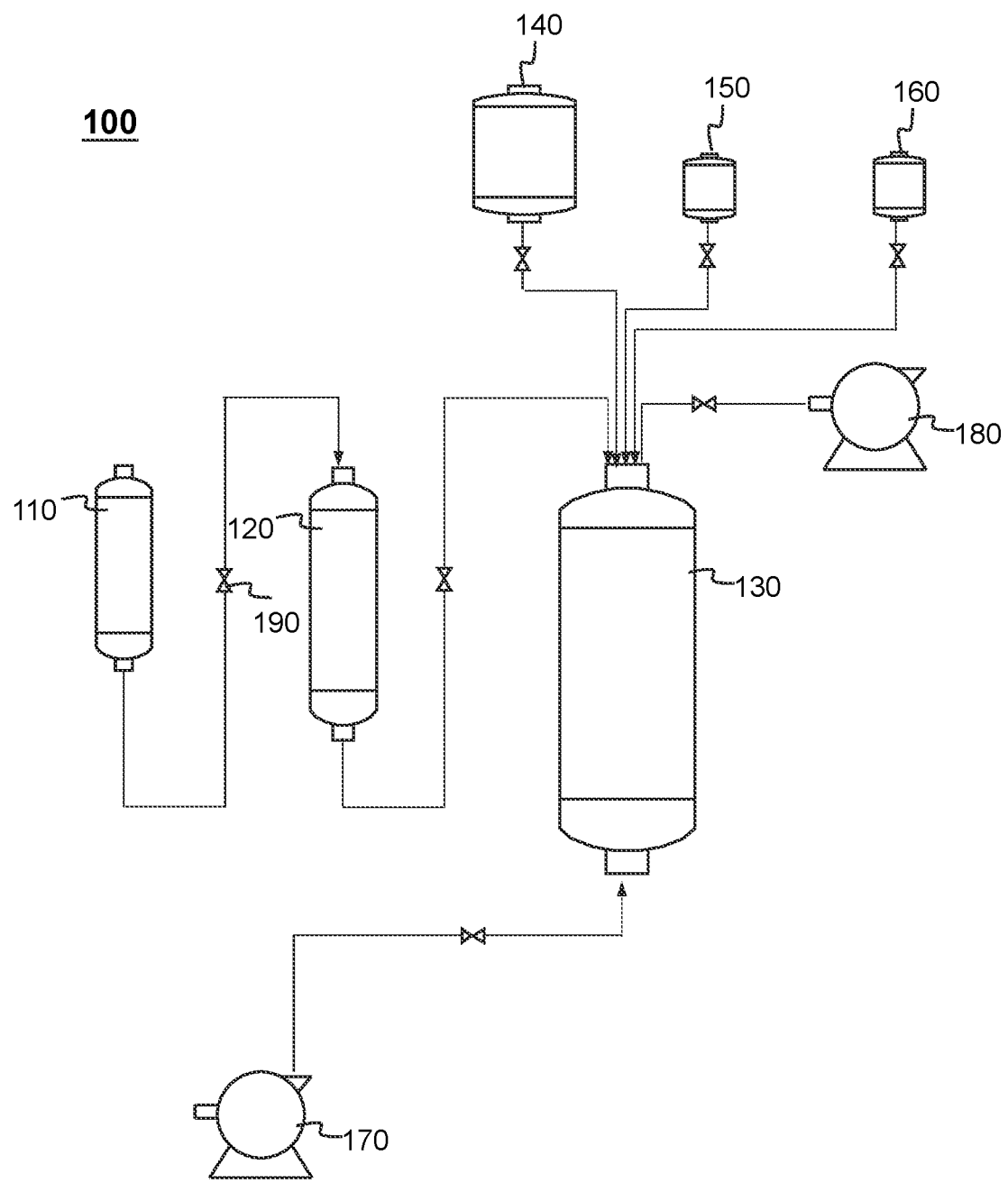
FIG. 1 is a schematic diagram illustrating an exemplary fermentation system 100 according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented in a different order. Conversely, the operations may be implemented in inverted order or simultaneously. Moreover, one or more other operations may be added to the flowcharts. One or more operations may be removed from the flowcharts.

As used herein, the term "tank" of the present disclosure may refer to a tank of various shapes and volume capacities. For example, the shape of the tank may be a cylinder shape, a cubic shape, a hemisphere shape, a trapezoid shape, a semi-ellipsoidal shape, a straight prism shape, an inclined prism shape, a truncated cone shape, a truncated pyramid shape, a truncated tetrahedron shape, an irregular shape, or the like, or a combination thereof. In some embodiments, the volume capacity of the tank may range from 0.5 L-2000 m$^3$, or more, or less. In some embodiments, the tank may be a seed tank for growing a seed culture or a fermentation tank for growing a microbial culture. In some embodiments, the tank may be used to store materials that need to be added to the fermentation tank, such as supplementary nutrient materials (e.g., fermentation culture, etc.), pH adjusting agents, D-amino acid, antifoaming agents, or the like, or any combination thereof.

As used herein, the term "concentration of carbon dioxide ($CO_2$)" may refer to a volume concentration of $CO_2$ in the exhaust gas of the microbial culture. In some embodiments, the concentration of $CO_2$ may be represented as a volume percentage of $CO_2$ in the exhaust gas, such as 5%, 8%, etc. Other means of representing the concentration of $CO_2$ may also be implemented in connection with the methods provided by the present disclosure. For example, the concentration of $CO_2$ may be represented as a volume ratio of $CO_2$ in the exhaust gas, such as 0.05, 0.08.

As used herein, the term "concentration of lactate" of the present disclosure may refer to a concentration of lactate in a microbial culture in a fermentation tank. In some embodiments, the concentration of lactate in the microbial culture may be represented as a mass concentration of the lactate of the microbial culture (e.g., mass in a unit volume), such as 20 mg/L, 30 mg/L. Other means of representing the concentration of lactate in the microbial culture may also be implemented in connection with the methods provided by the present disclosure. For example, the concentration of lactate in the microbial culture may be represented as a mole concentration of the lactate of the microbial culture, such as 0.2 mM/L, 0.3 mM/L.

FIG. 1 is a schematic diagram illustrating an exemplary fermentation system 100 according to some embodiments of the present disclosure. The fermentation system 100 may include one or more devices related to a fermentation production process. As shown in FIG. 1, the fermentation system 100 may include one or more seed tanks (e.g., the first seed tank 110, the second seed tank 120), a fermentation tank 130, a supplementary material tank 140, a pH adjusting agent tank 150, a D-amino acid tank 160, one or more pumps (e.g., the first pump 170, the second pump 180), and one or more regulators 190. It should be noted that some of the elements shown herein may or may not physically exist if the functions can be carried out properly. For example, the term "pump" may refer to a device or mechanism that utilizes and/or develops differential pressure to transfer materials (e.g., slurries, solids, liquids, gases, etc.) and/or momentum. In certain embodiments, there may be physical pressure-developing devices. In certain embodiments, materials can be transferred by existing pressure differences.

The one or more seed tanks may be configured to obtain a target seed culture using a single microorganism or a microorganism strain before a fermentation production process in the fermentation tank 130 starts. As used herein, the term "target seed culture" of the present disclosure may refer to a microbial culture in which the microbes have relatively high biological activities and the concentration of microbes reaches a required concentration of microbes for inoculating the microbes to a fermentation medium. Merely by way of example, a bacterial strain may be used in the fermentation production process to obtain a target product (e.g., $CoQ_{10}$). An exemplary bacterial strain is *Rhodobacter sphaeroides*. For instance, before a fermentation production process starts in the fermentation tank 130, a target microbial suspension may be prepared using the single microorganism or the microorganism strain. The target microbial suspension may be inoculated in a first seed medium in the first seed tank 110. The microbes in the first seed medium may be cultured for a first predetermined time period (e.g., 24 h, 30 h) to obtain a first seed culture. In some embodiments, the first seed culture may be used as the target seed culture. In some embodiments, the first seed culture may be inoculated to a second seed medium in the second seed tank 120. The microbes in the second seed medium may be cultured for a second predetermined time period (e.g., 24 h, 30 h) to obtain a second seed culture. In some embodiments, the second seed culture may be used as the target seed culture. In some embodiments, the second seed culture may be inoculated in a third seed medium in a third seed tank, and the microbes in the third seed culture may be cultured to obtain a third seed culture. The third seed culture may be used as the target seed culture. Similar operations may be performed for a plurality of times to obtain the target seed culture. The one or more seed tanks may be connected via a pipe. For example, a portion of the first seed culture may be moved from the first seed tank 110 to the second seed tank 120 via the pipe. The seed tank in which the target seed culture is produced (e.g., the second seed tank 120) may be connected to the fermentation tank 130 via a pipe. For instance, a portion of the second seed culture may be moved from the second seed tank 120 to the fermentation tank 130 via the pipe. In some embodiments, the one or more regulators 190 may be configured to control the flow rate and/or the total volume of the moved seed culture.

The fermentation production process may be conducted in the fermentation tank 130. The target seed culture may be inoculated to a fermentation medium in the fermentation tank 130 to obtain a microbial culture. The microbial culture may be grown in the fermentation tank 130 by providing a carbon source and an oxygen source and under appropriated conditions until one or more fermentation ending conditions are satisfied. The first pump 170 may be configured to pump gas into the microbial culture during the fermentation production process. The gas may include oxygen, nitrogen, and/or other types of gas. For example, the gas may be sterilized air. In an aerobic fermentation production process, the microbes may utilize the oxygen in the microbial culture for proliferation and normal metabolic activities (e.g., aerobic aspiration, synthesis of the target product). The second pump 180 may be configured to pump exhaust gas out of the fermentation tank 130 and control the tank pressure in the fermentation tank 130. The exhaust gas may include $CO_2$, oxygen, nitrogen, and/or other types of gas. In some embodiments, the power of the first pump 170 and/or the second pump 180 may be adjusted to control the flow rate of the gas and/or the exhaust gas. In some embodiments, the one or more regulators 190 may be configured to control the flow rate of the gas and/or the exhaust gas. The fermentation tank 130 may include one or more stirrers immersed in the microbial culture. For example, a stirrer may be configured to stir the microbial culture to uniformly mix various components of the microbial culture and promote the dissolution of the oxygen. The stirrer may be coupled to a rotor. A motor connected to the rotor may control the rotor speed to adjust the speed of the stirrer.

In some embodiments, one or more detectors may be included in the fermentation tank 130 or connected to the fermentation tank 130. The one or more detectors may be configured to detect one or more fermentation parameters at predetermined time intervals during the fermentation production process. For instance, the one or more fermentation parameters may include temperature of the microbial culture, tank pressure, pH, a total volume of the microbial culture, a viscosity of the microbial culture, a total concentration of living microbes and dead microbes in the microbial culture, a concentration of carbon source (e.g., glucose) in the microbial culture, a concentration of lactate in the microbial culture, a concentration of $CO_2$, or the like, or a combination thereof. During the $CoQ_{10}$ fermentation process, different oxygen supply level may have a great impact on the growth of the microbial culture and synthesis of coenzyme $Q_{10}$. Conventional fermentation parameters, such as pH, dissolved oxygen (DO) level, the concentration of saccharides, etc., cannot reflect the actual oxygen consumption level of the microbes in real time. The oxygen supply level, the growth rate, and the saccharides consumption rate of the microbes may be different in different periods, and the concentration of carbon dioxide released by the microbes may be also different in different periods. The lactate concentration of the fermentation broth is also different. The monitoring of carbon dioxide concentration and lactate concentration may be used to monitor the metabolism of the microbes in the fermentation process in real time. Real-time feedback adjustment based on carbon dioxide concentration and lactate concentration may achieve a reasonable and effective process control.

The supplementary nutrient material tank 140, the pH adjusting agent tank 150, and the D-amino acid tank 160 may be connected to the fermentation tank 130 via a pipe, respectively.

The supplementary nutrient material tank 140 may store supplementary nutrient materials. The supplementary nutrient materials may include but are not limited to a carbon source, a nitrogen source, a phosphorus source, a promoting factor, a mineral salt, a supplementary fermentation medium, or the like. For illustration purposes, only one supplementary nutrient material tank 140 is shown in FIG.

1. It should be noted that there may be multiple supplementary nutrient material tanks 140 storing various supplementary nutrient materials, and each of the multiple supplementary nutrient material tanks 140 may be connected to the fermentation tank 130. In some embodiments, the supplementary nutrient material tank 140 may further include a carbon source tank, a nitrogen source tank, a phosphorus source tank, a promoting factor tank, a mineral salt tank, a supplementary fermentation medium tank, or the like, or a combination thereof, which are not shown in FIG. 1. The carbon source tank may store an aqueous solution of carbon source, including but not limited to glucose, maltose, sucrose, starch, or the like, or a combination thereof. The nitrogen source tank may store an aqueous solution of a nitrogen source, such as ammonia, ammonium sulfate, ammonium nitrate, urea, corn steep liquor, or the like, or a combination thereof. The phosphorus source tank may store an aqueous solution of a phosphorus source, such as monopotassium phosphate, dipotassium phosphate, or the like. The promoting factor tank may store an aqueous solution of a promoting factor, including but not limited to vitamins, amino acids, steroids, solanesol, p-hydroxybenzoic acid, beta-carotene, or the like. The promoting factors may be added to the microbial culture to promote the proliferation of the microbes, regulate the metabolic activities of the microbes, and/or the production of the target product, or the like. The mineral salt tank may store one or more types of mineral salt, including but not limited to an aqueous solution of a sulfate, a chlorate, or a phosphate of sodium, potassium, magnesium, iron, copper, zinc, manganese, or the like, or a combination thereof. In some embodiments, an inorganic salt may also serve as a nitrogen source (e.g., ammonium sulfate), and/or a phosphate source (e.g., monopotassium phosphate). In some embodiments, a supplementary nutrient material may both serve as a carbon source and a nitrogen source, such as the corn steep liquor. The supplementary fermentation medium may store a supplementary fermentation medium, including but not limited to a carbon source, a nitrogen source, a phosphate source, a promoting factor, a mineral salt, or the like, or a combination thereof. Merely by way of example, 1 L of the supplementary fermentation medium may be prepared using 10 g of glucose, 5 g of yeast extract, 5 g of peptone, 5 g of NaCl, 2 g of $CaCl_2$), 0.5 g of $(NH_4)_2SO_4$, 1 μg of vitamin $B_1$, 1 μg vitamin K, 1.5 μg of vitamin A, 0.6 μg of $CuSO_4.5H_2O$, 0.8 μg of $Na_2MoO_4.2H_2O$, 1.2 μg of $ZnSO_4.7H_2O$, 0.33 μg $KNO_3$, 0.44 μg NaBr. In some embodiments, the supplementary nutrient materials stored in the one or more supplementary nutrient material tank 140 may be added to the fermentation tank 130 when in need. For instance, at least a portion of a supplementary nutrient material may be added to the microbial culture in the fermentation tank 130 when the concentration of the supplementary nutrient material or one or more fermentation parameters are less than a preset concentration, or after a certain time period of growing the microbial culture, etc. As another example, one or more supplementary nutrient materials may be continuously added to the fermentation tank at a predetermined supply rate or a varying supply rate based on the current time period.

The pH adjusting agent tank 150 may store pH adjusting agents, which may include but not be limited to an aqueous solution of acid (e.g., phosphoric acid) or a derivative thereof (e.g., phosphate), an aqueous solution of alkaline or a derivative thereof, or a buffer solution. In some embodiments, there may be multiple pH adjusting agent tanks 150 for storing various pH adjusting agents, such as one or more acid tanks, one or more alkaline tanks, one or more buffer solution tanks. For example, the acid may include but is not limited to acetic acid, phosphoric acid, hydrochloric acid, sulfuric acid, nitric acid, oxalic acid, or the like, or any combination thereof. As another example, the alkaline may include but is not limited to ammonia, urea, potassium hydroxide, sodium hydroxide, or the like, or any combination thereof. The buffer solution may include but is not limited to monopotassium phosphate, dipotassium phosphate, monosodium phosphate, disodium phosphate, or the like, or a combination thereof. In some embodiments, when supplementary nutrient materials are added to the microbial culture, the buffer solution may also be added to the microbial culture, so as to help maintain the pH of the microbial culture at a required range (e.g., 5.5-8.5). When the pH of the microbial culture does not satisfy a predetermined pH condition, a portion of the pH adjusting agents (e.g., acid or alkaline) may be added to the microbial culture to adjust the pH of the microbial culture. In some embodiments, a carbon source stored in the carbon source tank and/or a nitrogen source stored in a nitrogen source tank may be added to the microbial culture to adjust the pH of the microbial culture via regulating the metabolic activities of the microbes. In some embodiments, the nitrogen source may be an alkaline (e.g., an aqueous solution of ammonia) and may be used to directly increase the pH of the microbial culture.

The D-amino acid tank 160 may be configured to store one or more types of D-amino acid (e.g., in the form of an aqueous solution of D-amino acid). During a controlled fermentation production process, the microbes may be encased by extracellular polymeric substances (EPS) and form biofilms, which may significantly affect the transfer efficiency of materials (e.g., oxygen, the carbon source, the nitrogen source, the phosphate source, etc.) between the microbes and the fermentation medium. Thus, the production of the target product may be greatly affected. In order to prevent, remove, reduce, disperse, disrupt, or eradicate biofilms in the microbial culture, D-amino acid may be added to the microbial culture. The D-amino acid may include but is not limited to D-tyrosine, D-aspartic acid, D-arginine, D-methionine, D-leucine, D-tryptophan, D-phenylalanine, D-asparagine, D-glutamine, D-serine, D-glycine, D-lysine, D-cysteine, D-histidine, D-valine, D-proline, D-isoleucine, D-threonine, D-glutamic acid, D-alanine, or the like, or a combination thereof, depending on the microbes used in the controlled fermentation production process. For example, in a controlled $CoQ_{10}$ fermentation production process using *Rhodobacter sphaeroides*, the D-amino acid may include one or more of D-tyrosine, D-aspartic acid, D-arginine, D-methionine, D-leucine, D-tryptophan, and D-phenylalanine. In some embodiments, the biofilms may cause one or more fermentation parameters to change. For instance, due to the inhibition of the transfer of oxygen between the microbes and the fermentation medium, the concentration of $CO_2$ in the exhaust gas of the microbial culture may be decreased and/or the concentration of lactate in the microbial culture may be increased. When one or more fermentation parameters that are affected by the biofilms (e.g., the concentration of lactate in the microbial culture and/or the concentration of $CO_2$ in the exhaust gas of the microbial culture) do not satisfy a set of parameter conditions, the D-amino acid can be added to the microbial culture to prevent, remove, reduce, disperse, disrupt, or eradicate biofilms in the microbial culture. Thus, the transfer efficiency of materials between the microbes and the fermentation medium may be improved. In some embodiments, the one or more regulators 190 may be configured to control the supply rate of the supplementary nutrient materials, the pH adjusting agent and/or the D-amino acid.

In some embodiments, the one or more detectors may generate signals encoding the one or more fermentation parameters. The signals may be transmitted to a processing device and/or a terminal device. The processing device may be configured to monitor the one or more fermentation parameters. For instance, the processing device may obtain a set of parameter conditions corresponding to the one or more fermentation parameters. The processing device may determine whether the one or more fermentation parameters satisfy the set of parameter conditions. If the one or more fermentation parameters do not satisfy the set of parameter conditions, the processing device may send a prompt message to the terminal device, and/or generate one or more controlling signals to perform one or more operations to adjust the one or more parameter conditions. For example, when the concentration of lactate in the microbial culture does not satisfy the set of parameter conditions, the processing device may transmit a control signal to one or more components of the fermentation system 100 (e.g., one or more regulators 190) to adjust the rotor speed, the gas supply rate, the tank pressure, or the like, or a combination thereof. The terminal device may receive signals encoding the one or more fermentation parameters and display a diagram and/or a chart showing how the one or more fermentation parameters change over time on a screen of the terminal device. For instance, the diagram may include a curve graph, a straight line graph, or the like, or a combination thereof. The terminal device may also display the prompt message to notify a user (e.g., an operator) that the one or more fermentation parameters do not satisfy the set of parameter conditions. For example, the operator may input an instruction via the terminal device to perform the one or more operations to adjust the one or more fermentation conditions. Additionally or alternatively, the operator may manually manipulate the one or more components of the fermentation system 100 to adjust the one or more fermentation conditions. In some embodiments, the processing device and the terminal device may be integrated into a single device.

Merely for purpose of illustration, only one fermentation tank 130 is shown in FIG. 1. It should be noted that the fermentation system 100 may include multiple fermentation tanks 130. In some embodiments, each fermentation tank 130 may be connected to a second seed tank 120, a supplementary nutrient material tank 140, a pH adjusting agent tank 150, a D-amino acid tank 160, a first pump 170, and a second pump 180. In some embodiments, the fermentation production processes in multiple fermentation tanks 130 may be controlled, respectively. For example, the one or more fermentation parameters in the microbial culture in each fermentation tank may be monitored and controlled, respectively. In some embodiments, each fermentation tank 130 may be connected to at least one other fermentation tank 130, a supplementary nutrient material tank 140, a pH adjusting agent tank 150, a D-amino acid tank 160, a first pump 170, and a second pump 180. When the one or more parameter conditions do not satisfy the set of parameter conditions, a portion of the microbial culture in a first fermentation tank 130 may be moved to a second fermentation tank 130. For example, 5-60% (volume percentage) of the microbial culture in the first fermentation tank 130 may be moved to the second fermentation tank 130. The supplementary nutrient materials may be added to the microbial culture in the first fermentation tank 130 and the second fermentation tank 130. The microbial culture in the first fermentation tank 130 and the second fermentation tank 130 may be grown under appropriate conditions. The fermentation production processes in the first fermentation tank 130 and the second fermentation tank 130 may be controlled, respectively. Similar operations related to transferring the microbial culture may be performed for one or more times.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 2:
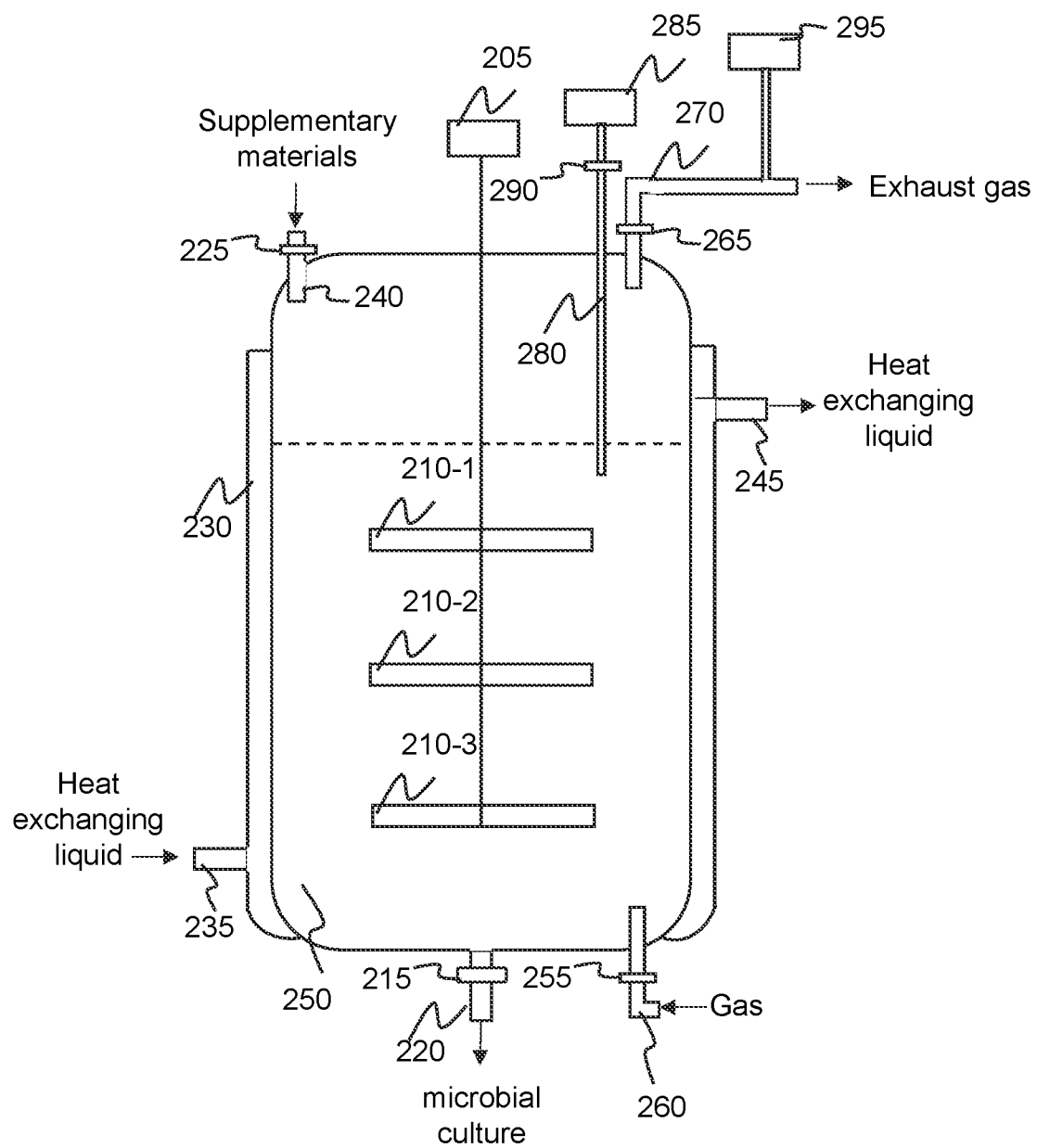
FIG. 2 is a schematic diagram illustrating an exemplary fermentation tank according to some embodiments of the present disclosure.

FIG. 2 is a schematic diagram illustrating an exemplary fermentation tank according to some embodiments of the present disclosure. A controlled fermentation production process may be conducted in the fermentation tank.

As shown in FIG. 2, the fermentation tank may include one or more stirrers (e.g., a stirrer 210-1, a stirrer 210-2, and a stirrer 210-3) immersed in a microbial culture 250. The microbial culture 250 may include various components, such as microbes, a fermentation medium, dissolved oxygen, supplementary nutrient materials, D-amino acid, antifoaming agents, metabolites of the microbes, or the like, or any combination thereof. In some embodiments, the metabolites of the microbes may include lactate, proteins, extracellular polymeric substances (EPS), dissolved $CO_2$, the target product (e.g., $CoQ_{10}$), or the like, or a combination thereof. The one or more stirrers may be configured to stir the microbial culture to uniformly mix various components of the microbial culture and promote the dissolution of the oxygen. A stirrer may be coupled to a rotor. A motor 205 may be connected to the rotor and may control the rotor speed to adjust the speed of the stirrer. The fermentation tank may include one or more supplementary material inlets 240. The supplementary materials may be added to the microbial culture 250 through the one or more supplementary material inlets 240, respectively. For example, the supplementary materials may include supplementary nutrient materials (e.g., a carbon source, a nitrogen source, a phosphorus source, a promoting factor, an mineral salt, a supplementary fermentation medium, etc.), a pH adjusting agent (e.g., an aqueous solution of acid or alkaline), D-amino acid, an antifoaming agent, or the like, or a combination thereof. In some embodiments, a portion of the microbial culture 250 may be moved from a first fermentation tank to a second fermentation tank through the microbial culture outlet 220. In some embodiments, when the fermentation production process is ended, the microbial culture 250 may be removed from the fermentation tank through the microbial culture outlet 220. In some embodiments, the microbial culture 250 may be continuously removed from the fermentation tank through the microbial culture outlet 220, while the supplementary nutrient materials may be continuously added to the microbial culture through the supplementary material inlet 240. The exhaust gas may be pumped out of the fermentation tank through a gas outlet 270. In some embodiments, the temperature of the microbial culture 250 may be controlled using a heat exchanging liquid (e.g., water). For example, the outer surface of the fermentation tank may be surrounded by a heat exchanging chamber 230. The heat exchanging liquid may be configured to flow into the heat exchange chamber 230 through the heat exchanging liquid inlet 235 and flow out of the heat change chamber 230 through the heat exchanging liquid outlet 245. The heat exchanging liquid may be recycled.

In some embodiments, the fermentation tank may be connected to one or more detector assemblies, such as a first detector assembly 285 and a second detector assembly 295. The first detector assembly 285 may be configured to measure one or more parameter conditions by taking a sample from the microbial culture 250. For instance, a sampling tube 280 may be used to take a sample from the microbial culture 250 and transfer the sample to the first detector assembly 285 at predetermined time intervals. The sample regulator 290 may be configured to control the flow rate or a total volume of the sample to be taken. The first detector assembly 285 may measure the one or more fermentation parameters by analyzing the components of the sample. Exemplary predetermined time intervals may be 0.5 h, 1 h, 1.5 h, etc. As used herein, if a sample is taken from the microbial culture 250 at a relatively short time interval (e.g., less than 3 min, 5 min, or the like), and the measurement time for the one or more fermentation parameter is also relatively short (e.g., less than 3 min, 5 min, or the like), the measurement of the one or more fermentation parameters may be considered as performed in real-time. In some embodiments, the first detector assembly 285 may include one or more detectors for measuring a total concentration of living microbes and dead microbes in the microbial culture, a concentration of carbon source (e.g., glucose) in the microbial culture, a concentration of lactate in the microbial culture, or the like, or a combination thereof. For instance, the first detector assembly 285 may include an enzyme electrode for detecting the concentration of lactate in the microbial culture. In some embodiments, the second detector assembly 295 may be configured to analyze concentration(s) of one or more components of the exhaust gas using a sample from the exhaust gas at predetermined time intervals. For instance, the second detector assembly 295 may be configured to measure a concentration of $CO_2$ in the exhaust gas (also referred to as a "concentration of $CO_2$ in the microbial culture"), a concentration of other gases in the exhaust gas, or the like, or a combination thereof. Merely by way of example, the second detector assembly 295 may include a mass spectrometer, a gas analyzer, etc. The gas analyzer may include a sensor including but not limited to an infrared sensor, a solid electrolyte sensor, a capacitance sensor, an optical fiber sensor. The fermentation tank may also include other detectors, such as a pH meter, a thermometer, a pressure gauge, or the like, or a combination thereof. In some embodiments, the one or more detectors in the first detector assembly 285 or the second detector assembly 295 may be one or more individual devices connected to the sampling tube.

In some embodiments, the first detector assembly 285, the second detector assembly 295, and/or other detectors may generate signals encoding the one or more fermentation parameters and transmit the signals to a processing device and/or a terminal device as described in connection with FIG. 1. The fermentation production process may be controlled based on the one or more fermentation parameters. If the one or more fermentation parameters do not satisfy a set of parameter conditions, the processing device and/or the terminal device may transmit control signals to one or more components to adjust the one or more fermentation parameters. In some embodiments, the control signals are automatically generated by preset protocols. In some embodiments, the control signals are generated by operators of the fermentation production process. In some embodiments, when the concentration of $CO_2$ in the exhaust gas of the microbial culture and/or the concentration of lactate in the microbial culture do/does not satisfy a first set of fermentation parameters, the control signals may be transmitted to the motor 205 for adjusting the rotor speed, to the gas regulator 255 for adjusting the air supply rate, and/or to the exhaust gas regulator 265 for adjusting the tank pressure. In some embodiments, when the concentration of $CO_2$ in the exhaust gas of the microbial culture and/or the concentration of lactate in the microbial culture do/does not satisfy a second set of fermentation parameters, the control signals may be transmitted to the microbial culture regulator 215 to cause the microbial culture regulator 215 to transfer a portion of the microbial culture 250 (e.g., 5-60%) to another fermentation tank. In some embodiments, when the concentration of $CO_2$ in the exhaust gas of the microbial culture and/or the concentration of lactate in the microbial culture do/does not satisfy a third set of fermentation parameters, the control signals may be transmitted to the supplementary regulator 225 to cause the D-amino acid to be added in the microbial culture 250 to prevent, remove, reduce, disperse, disrupt, or eradicate biofilms in the microbial culture. Details regarding the control of the fermentation production processes based on the concentration of $CO_2$ in the exhaust gas of the microbial culture and/or the concentration of lactate in the microbial culture may be found elsewhere in the present disclosure, for example, in FIGS. 4-7 and the description thereof.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 3:
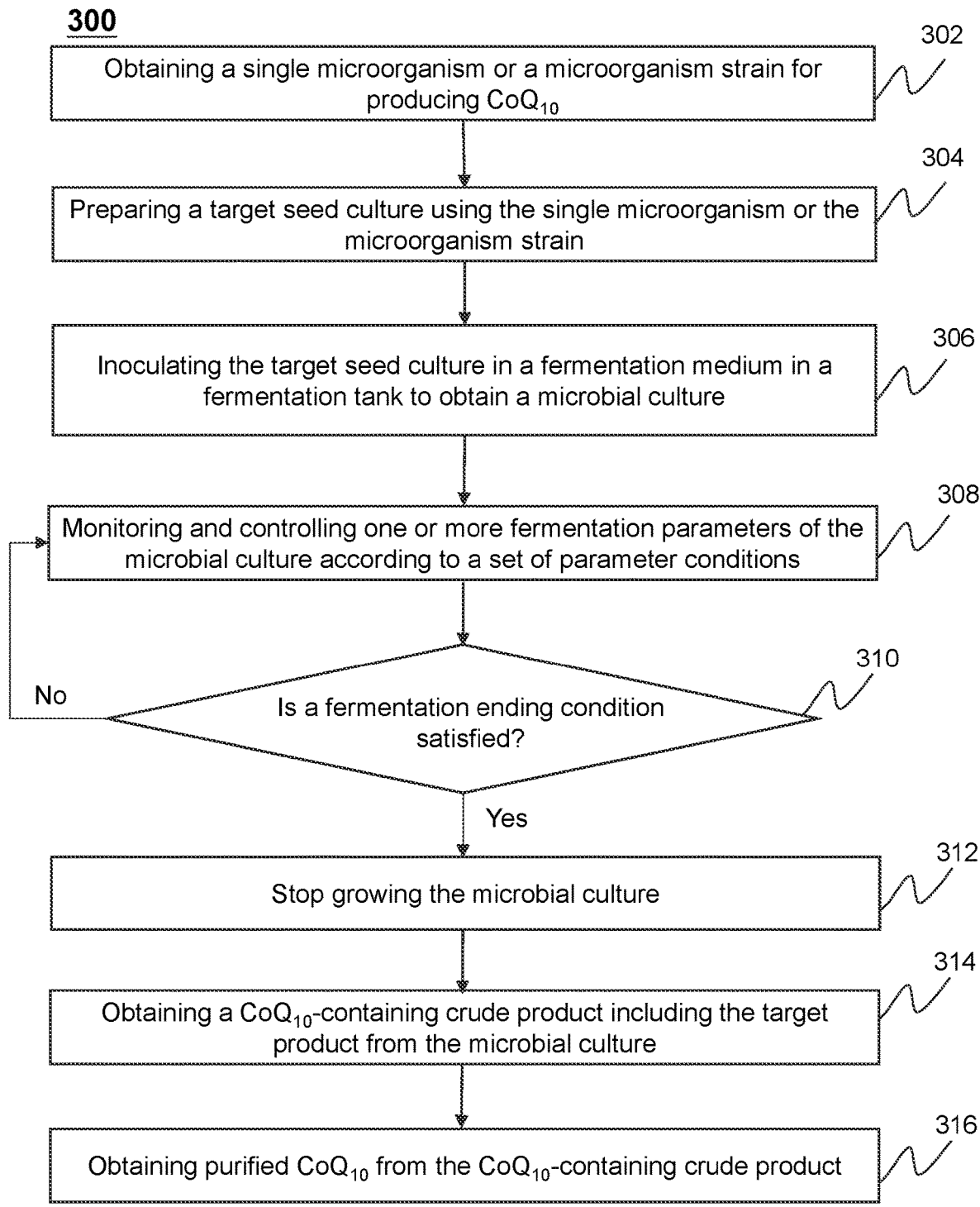
FIG. 3 is a flowchart illustrating an exemplary process for producing $CoQ_{10}$ through a controlled fermentation production process according to some embodiments of the present disclosure.

FIG. 3 is a flowchart of an exemplary process for producing $CoQ_{10}$ through a controlled fermentation production process according to some embodiments of the present disclosure.

In 302, a single microorganism or a microorganism strain for producing $CoQ_{10}$ may be obtained. The microorganism for producing $CoQ_{10}$ as mentioned above to be used in the present disclosure may include but is not limited to bacteria, yeast, fungi, a single cell or a plurality of cells of an animal or a plant, or the like, or any combination thereof. For example, the microorganism for producing $CoQ_{10}$ may include a single microorganism or a microorganism strain of the genus *Agrobacterium*, the genus *Aspergillus*, the genus *Acetobacter*, the genus *Aminobacter*, the genus *Agromonas*, the genus *Acidiphilium*, the genus *Bulleromyces*, the genus *Bullera*, the genus *Brevundimonas*, the genus *Cryptococcus*, the genus *Chionosphaera*, the genus *Candida*, the genus *Cerinosterus*, the genus *Exisophiala*, the genus *Exobasidium*, the genus *Fellomyces*, the genus *Filobasidiella*, the genus *Filobasidium*, the genus *Geotrichum*, the genus *Graphiola*, the genus *Gluconobacter*, the genus *Kockovaella*, the genus *Kurtzmanomyces*, the genus *Lalaria*, the genus *Leucosporidium*, the genus *Legionella*, the genus *Methylobacterium*, the genus *Mycoplana*, the genus *Oosporidium*, the genus *Pseudomonas*, the genus *Psedozyma*, the genus *Paracoccus*, the genus *Petromyces*, the genus *Rhodotorula*, the genus *Rhodosporidium*, the genus *Rhizomonas*, the genus *Rhodobium*, the genus *Rhodoplanes*, the genus *Rhodopseudomonas*, the genus *Rhodobacter*, the genus *Sporobolomyces*, the genus *Sporidiobolus*, the genus *Saitoella*, the genus *Schizosaccharomyces*, the genus *Sphingomonas*, the genus *Sporotrichum*, the genus *Sympodiomycopsis*, the genus *Sterigmatosporidium*, the genus *Tapharina*, the genus *Tremella*, the genus *Trichosporon*, the genus *Tilletiaria*, the genus *Tilletia*, the genus *Tolyposporium*, the genus *Tilletiopsis*, the genus *Ustilago*, the genus *Udeniomyces*, the genus *Xanthophilomyces*, the genus *Xanthobacter*, the genus *Paecilomyces*, the genus *Acremonium*, the genus *Hyhomonus*, and the genus *Rhizobium*.

In some embodiments, in terms of the culture easiness and productivity, bacteria (preferably non photosynthetic bacteria) and yeast may be used. As for the bacteria, for example, the genus *Agrobacterium*, the genus *Gluconobacter* and the like may be used. As for the yeast, for example, the genus *Schizosaccharomyces*, the genus *Saitoella* and the like may be used.

As for preferable species, the microbial cultures of the present disclosure may use, for example, *Agrobacterium tumefacience, Agrobacterium radiobacter, Aspergillus clavatus, Acetobacter xylinum, Aminobacter aganouensis, Agromonas oligotrophica, Acidiphilium multivorum, Bulleromyces albus, Bullera armeniaca, Brevundimonas diminuta, Cryptococcus laurentii, Chionosphaera apobasidialis, Candida curvata, Cerinosterus luteoalbus, Exisophiala alcalophila, Exobasidium gracile, Fellomyces fuzhouensis, Filobasidiella neoformans, Filobasidium capsuloigenum, Geotrichum capitatum, Graphiola cylindrica, Gluconobacter suboxydans, Kockovaella imperatae, Kurtzmanomyces nectairei, Lalaria cerasi, Leucosporidium scottii, Legionella anisa, Methylobacterium extorguens, Mycoplana ramosa, Oosporidium margaritiferum, Pseudomonas denitrificans, Pseudomonas shuylkilliensis, Psedozyma aphidis, Paracoccus denitrificans, Petromyces alliaceus, Rhodotorula glutinis, Rhodotorula minuta, Rhodosporidium diobovatum, Rhizomonas suberifaciens, Rhodobium orients, Rhodoplanes elegans, Rhodopseudomonas palustris, Rhodobacter capsulatus, Sporobolomyces holsaticus, Sporobolomyces pararoseus, Sporidiobolus johnsonii, Saitoella complicata, Schizosaccharomyces pombe, Sphingomonas parapaucimobilis, Sporotrichum cellulophilium, Sympodiomycopsis paphiopedili, Sterigmatosporidium polymorphum, Sphingomonas adhesiva, Tapharina caerulescens, Tremella mesenterica, Trichosporon cutaneum, Tilletiaria anomala, Tilletia caries, Tolyposporium bullatum, Tilletiopsis washintonesis, Ustilago esculenta, Udeniomyces megalosporus, Xanthophilomyces dendrorhous, Xanthobacter flavus, Paecilomyces lilacinus, Acremonium chrysogenum, Hyphomonas hirschiana, Rhizobium meliloti, Rhodopseudomonas capsulatus, Rhodopseudomonas gelatinosa, Pseudomonas aeruginosa, Pseudomonas denitrificans, Paracoccus denitrificans, Cryptococcus neoformans, Acetobacter, Agrobacterium tumefaciens, Protaminobacte, Rhizopus radiobacterium, Rhizobium leguminosarum, Rhodopseudomonas rubrum, Rhodobacter capsulatus, Rhodobacter sphaeroides, Rhodobacter suffidophilus, Cryptococcus neoformans, Aspergillus fumigatus, Ustilago zea*, or the like, or any combination thereof. A fugus strain may also be used for producing $CoQ_{10}$, such as *Bullera pseudoalba, Candida tropicalis, Sporobolomyces roseus*, etc. In the following description, as an example, a bacterial strain may be used for producing $CoQ_{10}$. An exemplary bacterial strain may be *Rhodobacter sphaeroides*. In some embodiments, the bacterial strain used for producing $CoQ_{10}$ through the fermentation production processes may be *Rhodobacter sphaeroides* JDW-610. The JDW-610 strain was obtained from the China General Microbiological Culture Collection Center (CGMCC). The preservation number for the JDW-610 strain is CGMCC No. 4497 and the preservation date for the JDW-610 strain is Dec. 21, 2010.

In some embodiments, the single microorganism or the microorganism strain may be a wild type. In some embodiments, the single microorganism or the microorganism strain may be a mutant type. For example, the single microorganism or the microorganism strain may be a mutant type that can increase the yield of $CoQ_{10}$, as compared to the wild type. In some embodiments, the single microorganism or the microorganism strain may be a genetically engineered microorganism or microorganism strain. For example, the single microorganism or the microorganism strain may be obtained by inserting one or more nucleotides, deleting one or more nucleotides, and/or replacing one or more nucleotides at a specific site in a nucleic acid sequence related to controlling the synthesis of $CoQ_{10}$. As another example, a DNA segment encoding $CoQ_{10}$ may be integrated into a DNA chain, and transferred to a microbial cell (e.g., *Escherichia coli*) to obtain the single microorganism or the microorganism strain for producing $CoQ_{10}$.

In 304, a target seed culture may be prepared using the single microorganism or the microorganism strain. For instance, a target microbial suspension may be prepared using the single microorganism or the microorganism strain. The target microbial suspension may be inoculated in a first seed medium in the first seed tank 110. The microbes (also referred to as "microorganisms") in the first seed medium may be cultured for a first predetermined time period (e.g., 24 h, 30 h) to obtain a first seed culture. In some embodiments, the first seed culture may be used as the target seed culture. In some embodiments, the first seed culture may be inoculated to a second seed medium in the second seed tank 120. The microbes in the second seed medium may be cultured for a second predetermined time period (e.g., 24 h, 30 h) to obtain a second seed culture. In some embodiments, the second seed culture may be used as the target seed culture. In some embodiments, similar operations may be performed to obtain a third seed culture as the target seed culture.

In 306, the target seed culture may be inoculated in a fermentation medium in a fermentation tank to obtain a microbial culture. For instance, a portion of the target seed culture may be moved to the fermentation tank via a pipe based on a preset volume ratio and the volume of the fermentation medium. The preset volume ratio may be a ratio of the volume of the moved target seed culture to the volume of the fermentation medium. For example, the preset volume ratio may be 12%. In some embodiments, the target seed culture may be inoculated in multiple fermentation tanks. The fermentation production process in each fermentation tank may be controlled, respectively. The fermentation medium may include one or more carbon sources, nitrogen sources, mineral salts, promoting factors, or the like, or a combination thereof. Merely by way of example, 1 L of the supplementary fermentation medium may be prepared using 10 g of glucose, 5 g of yeast extract, 5 g of peptone, 5 g of NaCl, 2 g of $CaCl_2$), 0.5 g of $(NH_4)_2SO_4$, 1 μg of vitamin $B_1$, 1 μg vitamin K, 1.5 μg of vitamin A, 0.6 μg of $CuSO_4.5H_2O$, 0.8 μg of $Na_2MoO_4.2H_2O$, 1.2 μg of $ZnSO_4.7H_2O$, 0.33 μg $KNO_3$, and 0.44 μg NaBr.

The microbial culture may be grown in the fermentation tank. In some embodiments, air may be continuously or discontinuously pumped into the microbial culture to provide oxygen for the microbes. The air may be sterilized air. In some embodiments, supplementary nutrient materials may be added to the microbial culture, such as a carbon source, a nitrogen source, a phosphorus source, a promoting factor, a mineral salt, a supplementary fermentation medium, or the like, or a combination thereof. For example, the carbon source may be a glucose solution, and the nitrogen source may be an aqueous solution of ammonia. The supplementary fermentation medium may include one or more carbon sources, nitrogen sources, mineral salts, promoting factors, or the like, or a combination thereof. The composition of the supplementary fermentation medium and the composition of the fermentation medium in the fermentation tank may be the same or different. In some embodiments, the microbial culture may be grown until a fermentation ending condition is satisfied.

In 308, one or more fermentation parameters of the microbial culture may be monitored and controlled according to a set of parameter conditions. For instance, one or more detectors may be configured to measure the one or more fermentation parameters at predetermined time intervals. Exemplary predetermined time intervals may be 2 min, 5 min, 10 min, 15 min, 0.5 h, 1 h, 1.5 h, etc. The one or more fermentation parameters may include temperature of the microbial culture, tank pressure, pH, a total volume of the microbial culture, a viscosity of the microbial culture, a total concentration of living microbes and dead microbes in the microbial culture, a concentration of lactate in the microbial culture, a concentration of $CO_2$ in an exhaust gas of the microbial culture (also referred to "concentration of $CO_2$ in the microbial culture"), or the like, or a combination thereof.

During the fermentation production process, a processing device may obtain the one or more fermentation parameters measured by the one or more detectors and control the one or more fermentation parameters according to a set of fermentation conditions. If the one or more fermentation parameters do not satisfy the set of fermentation conditions, one or more operations may be performed to adjust the one or more fermentation parameters, so as to control the fermentation production process. For example, a pH condition in the fermentation conditions may require the pH of the microbial culture to be maintained at pH 5.5-8.5. If the pH does not satisfy the fermentation parameters, a pH adjusting agent may be added to the microbial culture to increase or decrease the pH. In some embodiments, the set of parameter conditions may include one or more subsets of fermentation conditions related to the one or more fermentation parameters, respectively. Each subset of fermentation conditions may include a plurality of fermentation conditions corresponding to different time periods. For example, the subset of fermentation conditions corresponding to the concentration of $CO_2$ in the exhaust gas of the microbial culture may include: during 0-16 h of growing the microbial culture, the concentration of $CO_2$ in the exhaust gas of the microbial culture may be maintained at 0.5%-13%; during 16-48 h of growing the microbial culture, the concentration of $CO_2$ in the exhaust gas of the microbial culture may be maintained at 3%-15%; during 48-80 h of growing the microbial culture, the concentration of $CO_2$ in the exhaust gas of the microbial culture may be maintained at 3%-12%; and/or after 80 h of growing the microbial culture, the concentration of $CO_2$ in the exhaust gas of the microbial culture may be maintained at 2%-10%. As another example, the subset of fermentation conditions corresponding to the concentration of lactate in the microbial culture may include: during 0-16 h of growing the microbial culture, the concentration of lactate in the microbial culture may be maintained at 5-75 mg/L; during 16-48 h of growing the microbial culture, the concentration of lactate in the microbial culture may be maintained at 10-120 mg/L; during 48-80 h of growing the microbial culture, the concentration of lactate in the microbial culture is maintained at 20-180 mg/L; and/or after 80 h of growing the microbial culture, the concentration of lactate in the microbial culture may be maintained at 40-120 mg/L. If the concentration of lactate in the microbial culture and/or the concentration of $CO_2$ in the exhaust gas of the microbial culture do/does not satisfy the corresponding subset(s) of fermentation conditions, an operator of the fermentation production process may adjust rotor speed, tank pressure, and/or air supply rate, thereby adjusting the concentration of lactate in the microbial culture and/or the concentration of $CO_2$. For example, the carbon dioxide levels may be adjusted by adjusting the rotor speed, the tank pressure, and/or the air supply rate, or the like, or a combination thereof. As for another example, the lactate concentration may be adjusted by adjusting the rotor speed, the tank pressure, and/or the air supply rate, or the like, or a combination thereof.

In 310, a determination may be performed on whether a fermentation ending condition is satisfied. In some embodiments, the fermentation ending condition may include that the increasing speed of the total amount of $CoQ_{10}$ is less than a preset increasing speed threshold; a portion of the microbes have autolyzed, or the like, or any combination thereof. In some embodiments, one or more tests may be performed at preset time intervals after the microbial culture is grown for a certain time period (e.g., 80 h, 85 h) to determine whether the fermentation ending condition is satisfied. Exemplary preset time intervals may be 30 min, 1 h, etc. In some embodiments, the concentration of $CoQ_{10}$ in the sample of the microbial culture may be measured, for example, by High Performance Liquid Chromatography (HPLC). The total amount of produced $CoQ_{10}$ may be determined based on the measured concentration of $CoQ_{10}$ and the volume of the microbial culture. If the increasing speed of the total amount of the $CoQ_{10}$ is less than the preset increasing speed threshold, the fermentation ending condition may be satisfied. In some embodiments, a determination of whether a portion of the microbes has autolyzed may be performed based on a microscopic examination on a sample of the microbial culture. The sample of the microbial culture may be put on a glass slide and stained for observation via a microscope. If the color of the stained microbes turns lighter, a portion of the microbes may have autolyzed, and the fermentation ending condition may be satisfied. In some embodiments, the determination of whether a portion of the microbes has autolyzed may be performed based on a concentration of microbes in the microbial culture. If the concentration of microbes in the microbial culture is less than a preset concentration threshold, a portion of the microbes may have autolyzed. Methods for determining the concentration of microbes in the microbial culture may include but are not limited to using a counting chamber, a coulter counter, a flow cytometry, spectrophotometry, or a method based on staining and image analysis, a method based on impedance microbiology, or the like, or a combination thereof.

In some embodiments, the fermentation ending condition may include a predetermined time threshold. If the time for growing the microbial culture reaches the predetermined time threshold, the fermentation ending condition may be satisfied. In some embodiments, the predetermined time threshold may be determined based on a historical time period for growing the microbial culture in a historical controlled fermentation production process. For example, the historical time period may end when some of the microbes have autolyzed, when the color of the stained microbes becomes lighter in a microscopic examination, when the increasing speed of the total amount of $CoQ_{10}$ is less than a preset increasing speed threshold, or when the concentration of microbes in the microbial culture is less than a preset concentration threshold, or the like. As another example, the predetermined time threshold may be determined based on a historical time period corresponding to a relatively high economic benefit. In some embodiments, the predetermined time threshold may be determined using a prediction model based on a plurality of sample time periods for growing the microbial culture and the economic benefits corresponding to the sample time periods. Other fermentation ending conditions may also be implemented.

In 312, the growing of the microbial culture may be stopped. For instance, the supply of the air, the supplementary materials, the heat exchanging liquid, or the like may be stopped. The one or more detectors may stop measuring the one or more fermentation parameters. The processing device may stop monitoring the one or more fermentation parameters. In some embodiments, the microbial culture may be heated under a high tank pressure to inactivate the microbes in the microbial culture. For example, the microbial culture may be heated and/or a steam of high temperature may be supplied into the fermentation tank by which the microbes may be killed to stop the fermentation process. In some embodiments, at least portion of the microbial culture may be moved out from the fermentation tank during and/or after the heating process for subsequent $CoQ_{10}$ extracting process.

In 314, a $CoQ_{10}$-containing crude product may be obtained from the microbial culture. In some embodiments, the microbial culture containing $CoQ_{10}$ may be collected after the microbial culture is stopped. In some embodiments, a portion of the microbial culture containing $CoQ_{10}$ may be collected during the fermentation production process and the microbial culture may be heated to inactivate the microbes. The microbial culture containing $CoQ_{10}$ may be subjected to a cell wall disruption process to release the $CoQ_{10}$ from the microbial cells in the microbial culture. For instance, the method for disrupting cell walls may include using ultrasonic wave, using lysozyme, freezing and thawing the microbial culture, stirring the microbial culture intensely, using a strong acid (such as a concentrated hydrochloric acid), or the like, or a combination thereof. The $CoQ_{10}$-containing crude product may be obtained after the cell wall disruption process.

In 316, purified $CoQ_{10}$ may be obtained from the $CoQ_{10}$-containing crude product. In some embodiments, the purified $CoQ_{10}$ may be extracted from the $CoQ_{10}$-containing crude product through one or more extraction processes using a supercritical fluid and/or a solvent (e.g., one or more organic solvents). In some embodiments, the purified $CoQ_{10}$ may be obtained through membrane separation. In some embodiments, the purified $CoQ_{10}$ may be obtained through crystallization. Other methods of obtaining the purified $CoQ_{10}$ may also be implemented.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 4:
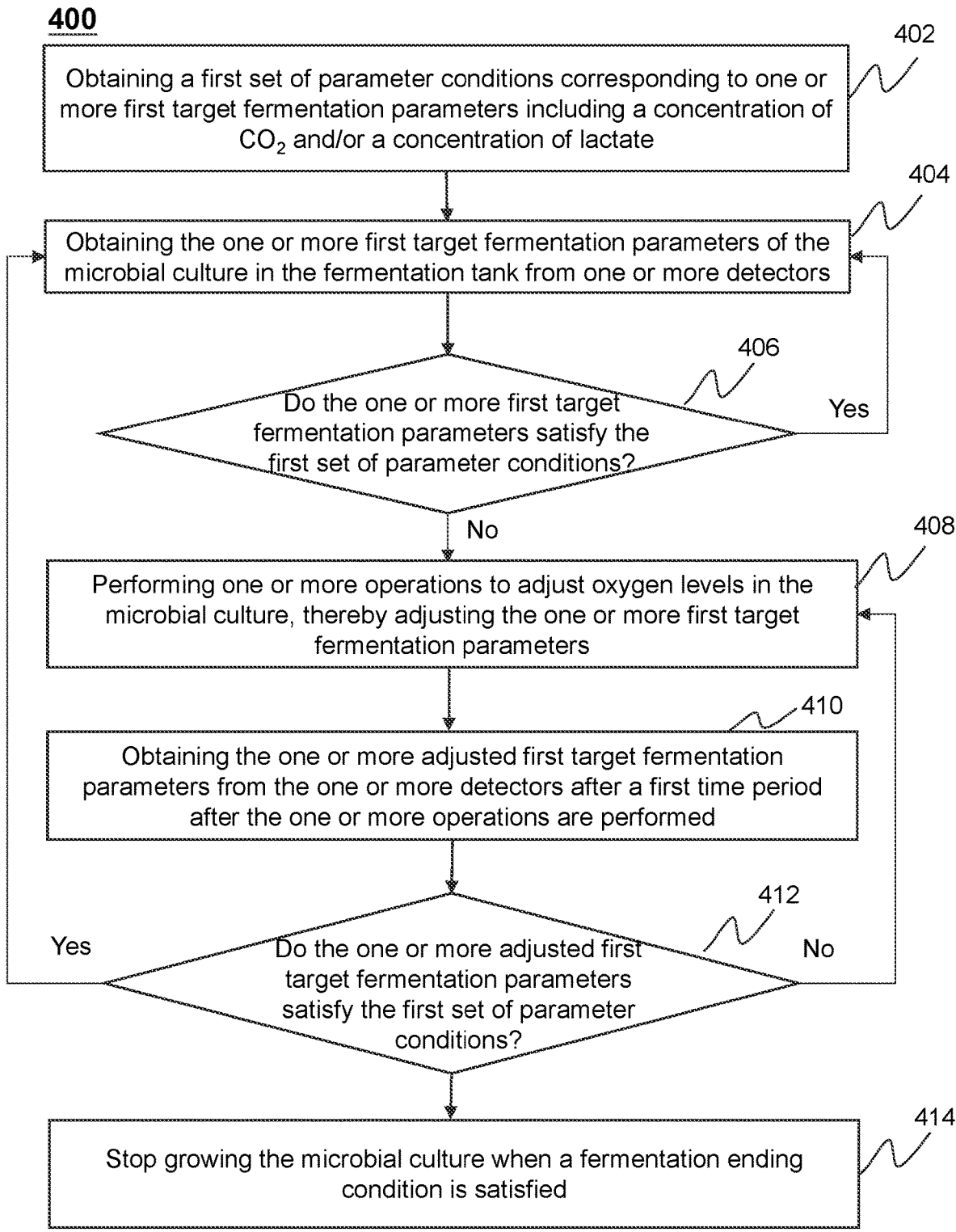
FIG. 4 is a flowchart illustrating an exemplary process for adjusting one or more first target fermentation parameters in a controlled $CoQ_{10}$ fermentation production process according to some embodiments of the present disclosure.

FIG. 4 is a flowchart of an exemplary process for growing a microbial culture based on one or more first target fermentation parameters in a controlled $CoQ_{10}$ fermentation production process according to some embodiments of the present disclosure. In some embodiments, the process 400 shown in FIG. 4 may be implemented in a controlled $CoQ_{10}$ fermentation production process in a fermentation tank with a volume capacity of 0.5 L-2000 m³. In some embodiments, the process 400 may be implemented in a controlled $CoQ_{10}$ fermentation production process in a fermentation tank with a volume capacity of 5 L-1000 m³. In some embodiments, the process 400 may be implemented in a controlled $CoQ_{10}$ fermentation production process in a fermentation tank with a volume capacity of 10 L-500 m³. In some embodiments, the process 400 may be implemented in a controlled $CoQ_{10}$ fermentation production process in a fermentation tank with a volume capacity of 100 L, 160 m³, 325 m³, or 500 m³.

In 402, a first set of parameter conditions corresponding to one or more first target fermentation parameters including a concentration of $CO_2$ and/or a concentration of lactate may be obtained. In some embodiments, the first set of parameter conditions may be stored in a storage device. The processing device may obtain the first set of parameter conditions from the storage device. In some embodiments, the first set of parameter conditions may include one or more first subsets of fermentation conditions correspond to the one or more first target fermentation parameters. Each of the one or more first subsets of fermentation conditions may include a plurality of fermentation conditions corresponding to different time periods.

In some embodiments, the first subset of fermentation conditions corresponding to the concentration of $CO_2$ in the exhaust gas of the microbial culture may include: during 0-16 h of growing the microbial culture, the concentration of $CO_2$ in the exhaust gas of the microbial culture may need to be maintained at 0.5%-13%; during 16-48 h of growing the microbial culture, the concentration of $CO_2$ in the exhaust gas of the microbial culture may need to be maintained at 3%-15%; during 48-80 h of growing the microbial culture, the concentration of $CO_2$ in the exhaust gas of the microbial culture may need to be maintained at 3%-12%; and/or after 80 h of growing the microbial culture, the concentration of $CO_2$ in the exhaust gas of the microbial culture may need to be maintained at 2%-10%.

In some embodiments, the first subset of fermentation conditions corresponding to the concentration of $CO_2$ in the exhaust gas of the microbial culture may include: during 0-16 h of growing the microbial culture, the concentration of $CO_2$ in the exhaust gas of the microbial culture may need to be maintained at 1%-10%; during 16-48 h of growing the microbial culture, the concentration of $CO_2$ in the exhaust gas of the microbial culture may need to be maintained at 5%-13%; during 48-80 h of growing the microbial culture, the concentration of $CO_2$ in the exhaust gas of the microbial culture may need to be maintained at 4%-10%; and/or after 80 h of growing the microbial culture, the concentration of $CO_2$ in the exhaust gas of the microbial culture may need to be maintained at 3%-8%.

In some embodiments, the first subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 0.5%-7%; during 8-16 h of growing the microbial culture, the concentration of $CO_2$ in the exhaust gas of the microbial culture may need to be maintained at 2%-13%; during 16-32 h of growing the microbial culture, the concentration of $CO_2$ in the exhaust gas of the microbial culture may need to be maintained at 3%-15%; during 32-48 h of growing the microbial culture, the concentration of $CO_2$ in the exhaust gas of the microbial culture may need to be maintained at 4%-13%; during 48-64 h of growing the microbial culture, the concentration of $CO_2$ in the exhaust gas of the microbial culture may need to be maintained at 3%-12%; during 64-80 h of growing the microbial culture, the concentration of $CO_2$ in the exhaust gas of the microbial culture may need to be maintained at 3%-10%; and/or after 80 h of growing the microbial culture, the concentration of $CO_2$ in the exhaust gas of the microbial culture may need to be maintained at 2%-9%.

In some embodiments, the first subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 1%-5%; during 8-16 h of growing the microbial culture, the concentration of $CO_2$ in the exhaust gas of the microbial culture may need to be maintained at 3%-10%; during 16-32 h of growing the microbial culture, the concentration of $CO_2$ in the exhaust gas of the microbial culture may need to be maintained at 5%-13%; during 32-48 h of growing the microbial culture, the concentration of $CO_2$ in the exhaust gas of the microbial culture may need to be maintained at 6%-11%; during 48-64 h of growing the microbial culture, the concentration of $CO_2$ in the exhaust gas of the microbial culture may need to be maintained at 5%-10%; during 64-80 h of growing the microbial culture, the concentration of $CO_2$ in the exhaust gas of the microbial culture may need to be maintained at 4%-9%; and/or after 80 h of growing the microbial culture, the concentration of $CO_2$ in the exhaust gas of the microbial culture may need to be maintained at 3%-8%.

In some embodiments, the first subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 0.5%-7%; and during a remaining time period of growing the microbial culture, the concentration of $CO_2$ in the exhaust gas of the microbial culture may need to be maintained at 2%-15%.

In some embodiments, the first subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 1%-5%; and during a remaining time period of growing the microbial culture, the concentration of $CO_2$ in the exhaust gas of the microbial culture may need to be maintained at 3%-13%.

In some embodiments, the first subset of fermentation conditions corresponding to the concentration of $CO_2$ in the exhaust gas of the microbial culture may include: during 8-16 h of growing the microbial culture, the concentration of $CO_2$ in the exhaust gas of the microbial culture may need to be maintained at 2%-13%; and during a remaining time period of growing the microbial culture, the concentration of $CO_2$ in the exhaust gas of the microbial culture may need to be maintained at 3%-15%.

In some embodiments, the first subset of fermentation conditions corresponding to the concentration of $CO_2$ in the exhaust gas of the microbial culture may include: during 8-16 h of growing the microbial culture, the concentration of $CO_2$ in the exhaust gas of the microbial culture may need to be maintained at 3%-10%; and during a remaining time period of growing the microbial culture, the concentration of $CO_2$ in the exhaust gas of the microbial culture may need to be maintained at 3%-13%.

In some embodiments, the first subset of fermentation conditions corresponding to the concentration of $CO_2$ in the exhaust gas of the microbial culture may include: during 16-32 h of growing the microbial culture, the concentration of $CO_2$ in the exhaust gas of the microbial culture may need to be maintained at 3%-15%; and during a remaining time period of growing the microbial culture, the concentration of $CO_2$ in the exhaust gas of the microbial culture may need to be maintained at 4%-13%.

In some embodiments, the first subset of fermentation conditions corresponding to the concentration of $CO_2$ in the exhaust gas of the microbial culture may include: during 16-32 h of growing the microbial culture, the concentration of $CO_2$ in the microbial culture may need to be maintained at 5%-13%; and during a remaining time period of growing the microbial culture, the concentration of $CO_2$ in the exhaust gas of the microbial culture may need to be maintained at 3%-11%.

In some embodiments, the first subset of fermentation conditions corresponding to the concentration of $CO_2$ in the exhaust gas of the microbial culture may include: during 32-48 h of growing the microbial culture, the concentration of $CO_2$ in the exhaust gas of the microbial culture may need to be maintained at 3%-15%; and during a remaining time period of growing the microbial culture, the concentration of $CO_2$ in the exhaust gas of the microbial culture may need to be maintained at 2%-13%.

In some embodiments, the first subset of fermentation conditions corresponding to the concentration of $CO_2$ in the exhaust gas of the microbial culture may include: during 32-48 h of growing the microbial culture, the concentration of $CO_2$ in the exhaust gas of the microbial culture may need to be maintained at 6%-11%; and during a remaining time period of growing the microbial culture, the concentration of $CO_2$ in the exhaust gas of the microbial culture may need to be maintained at 3%-10%.

In some embodiments, the first subset of fermentation conditions corresponding to the concentration of $CO_2$ in the exhaust gas of the microbial culture may include: during 48-64 h of growing the microbial culture, the concentration of $CO_2$ in the exhaust gas of the microbial culture may need to be maintained at 3%-12%; and during a remaining time period of growing the microbial culture, the concentration of $CO_2$ in the exhaust gas of the microbial culture may need to be maintained at 2%-10%.

In some embodiments, the first subset of fermentation conditions corresponding to the concentration of $CO_2$ in the exhaust gas of the microbial culture may include: during 48-64 h of growing the microbial culture, the concentration of $CO_2$ in the exhaust gas of the microbial culture may need to be maintained at 5%-10%; and during a remaining time period of growing the microbial culture, the concentration of $CO_2$ in the exhaust gas of the microbial culture may need to be maintained at 3%-9%.

In some embodiments, the first subset of fermentation conditions corresponding to the concentration of $CO_2$ in the exhaust gas of the microbial culture may include: during 64-80 h of growing the microbial culture, the concentration of $CO_2$ in the exhaust gas of the microbial culture may need to be maintained at 3%-10%; and during a remaining time period of growing the microbial culture, the concentration of $CO_2$ in the exhaust gas of the microbial culture may need to be maintained at 2%-9%.

In some embodiments, the first subset of fermentation conditions corresponding to the concentration of $CO_2$ in the exhaust gas of the microbial culture may include: during 64-80 h of growing the microbial culture, the concentration of $CO_2$ in the exhaust gas of the microbial culture may need to be maintained at 4%-9%; and during a remaining time period of growing the microbial culture, the concentration of $CO_2$ the microbial culture may need to be maintained at 3%-8%.

In some embodiments, the first subset of fermentation conditions corresponding to the concentration of lactate in the microbial culture may include: during 0-16 h of growing the microbial culture, the concentration of lactate in the microbial culture may need to be maintained at 5-75 mg/L; during 16-48 h of growing the microbial culture, the concentration of lactate in the microbial culture may need to be maintained at 10-120 mg/L; during 48-80 h of growing the microbial culture, the concentration of lactate in the microbial culture may need to be maintained at 20-180 mg/L; and/or after 80 h of growing the microbial culture, the concentration of lactate in the microbial culture may need to be maintained at 40-120 mg/L.

In some embodiments, the first subset of fermentation conditions corresponding to the concentration of lactate in the microbial culture may include: during 0-16 h of growing the microbial culture, the concentration of lactate in the microbial culture may need to be maintained at 10-50 mg/L; during 16-48 h of growing the microbial culture, the concentration of lactate in the microbial culture may need to be maintained at 20-100 mg/L; during 48-80 h of growing the microbial culture, the concentration of lactate in the microbial culture may need to be maintained at 30-150 mg/L; and/or after 80 h of growing the microbial culture, the concentration of lactate in the microbial culture may need to be maintained at 50-100 mg/L.

In some embodiments, the first subset of fermentation conditions corresponding to the concentration of lactate in the microbial culture may include: during 0-8 h of growing the microbial culture, the concentration of lactate in the microbial culture may need to be maintained at 5-50 mg/L; during 8-16 h of growing the microbial culture, the concentration of lactate in the microbial culture may need to be maintained at 8-75 mg/L; during 16-32 h of growing the microbial culture, the concentration of lactate in the microbial culture may need to be maintained at 10-80 mg/L; during 32-48 h of growing the microbial culture, the concentration of lactate in the microbial culture may need to be maintained at 20-120 mg/L; during 48-64 h of growing the microbial culture, the concentration of lactate in the microbial culture may need to be maintained at 20-160 mg/L; during 64-80 h of growing the microbial culture, the concentration of lactate in the microbial culture may need to be maintained at 30-180 mg/L; and/or after 80 h of growing the microbial culture, the concentration of lactate in the microbial culture may need to be maintained at 30-120 mg/L.

In some embodiments, the first subset of fermentation conditions corresponding to the concentration of lactate in the microbial culture may include: during 0-8 h of growing the microbial culture, the concentration of lactate in the microbial culture may need to be maintained at 10-30 mg/L; during 8-16 h of growing the microbial culture, the concentration of lactate in the microbial culture may need to be maintained at 10-50 mg/L; during 16-32 h of growing the microbial culture, the concentration of lactate in the microbial culture may need to be maintained at 20-50 mg/L; during 32-48 h of growing the microbial culture, the concentration of lactate in the microbial culture may need to be maintained at 30-100 mg/L; during 48-64 h of growing the microbial culture, the concentration of lactate in the microbial culture may need to be maintained at 30-150 mg/L; during 64-80 h of growing the microbial culture, the concentration of lactate in the microbial culture may need to be maintained at 50-150 mg/L; and/or after 80 h of growing the microbial culture, the concentration of lactate in the microbial culture may need to be maintained at 50-100 mg/L.

In some embodiments, the first subset of fermentation conditions corresponding to the concentration of lactate in the microbial culture may include: during 0-8 h of growing the microbial culture, the concentration of lactate in the microbial culture may need to be maintained at 5-50 mg/L; and during a remaining time period of growing the microbial culture, the concentration of lactate in the microbial culture is maintained at 8-180 mg/L.

In some embodiments, the first subset of fermentation conditions corresponding to the concentration of lactate in the microbial culture may include: during 0-8 h of growing the microbial culture, the concentration of lactate in the microbial culture may need to be maintained at 10-30 mg/L; and during a remaining time period of growing the microbial culture, the concentration of lactate in the microbial culture is maintained at 10-150 mg/L.

In some embodiments, the first subset of fermentation conditions corresponding to the concentration of lactate in the microbial culture may include: during 8-16 h of growing the microbial culture, the concentration of lactate in the microbial culture may need to be maintained at 8-75 mg/L; and during a remaining time period of growing the microbial culture, the concentration of lactate in the microbial culture is maintained at 10-180 mg/L.

In some embodiments, the first subset of fermentation conditions corresponding to the concentration of lactate in the microbial culture may include: during 8-16 h of growing the microbial culture, the concentration of lactate in the microbial culture may need to be maintained at 10-50 mg/L; and during a remaining time period of growing the microbial culture, the concentration of lactate in the microbial culture is maintained at 20-150 mg/L.

In some embodiments, the first subset of fermentation conditions corresponding to the concentration of lactate in the microbial culture may include: during 16-32 h of growing the microbial culture, the concentration of lactate in the microbial culture may need to be maintained at 10-80 mg/L; and during a remaining time period of growing the microbial culture, the concentration of lactate in the microbial culture is maintained at 20-180 mg/L.

In some embodiments, the first subset of fermentation conditions corresponding to the concentration of lactate in the microbial culture may include: during 16-32 h of growing the microbial culture, the concentration of lactate in the microbial culture may need to be maintained at 20-50 mg/L; and during a remaining time period of growing the microbial culture, the concentration of lactate in the microbial culture is maintained at 30-150 mg/L.

In some embodiments, the first subset of fermentation conditions corresponding to the concentration of lactate in the microbial culture may include: during 32-48 h of growing the microbial culture, the concentration of lactate in the microbial culture may need to be maintained at 20-120 mg/L; and during a remaining time period of growing the microbial culture, the concentration of lactate in the microbial culture is maintained at 20-180 mg/L.

In some embodiments, the first subset of fermentation conditions corresponding to the concentration of lactate in the microbial culture may include: during 32-48 h of growing the microbial culture, the concentration of lactate in the microbial culture may need to be maintained at 30-100 mg/L; and during a remaining time period of growing the microbial culture, the concentration of lactate in the microbial culture is maintained at 30-150 mg/L.

In some embodiments, the first subset of fermentation conditions corresponding to the concentration of lactate in the microbial culture may include: during 48-64 h of growing the microbial culture, the concentration of lactate in the microbial culture may need to be maintained at 20-160 mg/L; and during a remaining time period of growing the microbial culture, the concentration of lactate in the microbial culture is maintained at 30-180 mg/L.

In some embodiments, the first subset of fermentation conditions corresponding to the concentration of lactate in the microbial culture may include: during 48-64 h of growing the microbial culture, the concentration of lactate in the microbial culture may need to be maintained at 30-150 mg/L; and during a remaining time period of growing the microbial culture, the concentration of lactate in the microbial culture is maintained at 50-150 mg/L.

In some embodiments, the first subset of fermentation conditions corresponding to the concentration of lactate in the microbial culture may include: during 64-80 h of growing the microbial culture, the concentration of lactate in the microbial culture may need to be maintained at 30-180 mg/L; and during a remaining time period of growing the microbial culture, the concentration of lactate in the microbial culture is maintained at 30-120 mg/L.

In some embodiments, the first subset of fermentation conditions corresponding to the concentration of lactate in the microbial culture may include: during 64-80 h of growing the microbial culture, the concentration of lactate in the microbial culture may need to be maintained at 50-150 mg/L; and during a remaining time period of growing the microbial culture, the concentration of lactate in the microbial culture is maintained at 50-100 mg/L.

In 404, the processing device and/or the terminal device may obtain the one or more first target fermentation parameters of the microbial culture in the fermentation tank from one or more detectors. In some embodiments, a detector in the first detector assembly 285 may measure the concentration of lactate in the microbial culture at predetermined time intervals. For example, the detector may take a sample from the microbial culture and measure the concentration of lactate in the sample using an online lactate analyzer, such as BioPAT® Trace, SBA-60 Online Analysis and Control System, Biosen Lactate Analyzer, or the like. The online lactate analyzer may include but is not limited to an enzyme electrode, a microfluidic device with an integrated optical sensor, or the like, or a combination thereof. For instance, the enzyme electrode may include a film with immobilized enzymes, such as lactate dehydrogenase, lactate oxidase, etc. When a sample containing lactate flows through the film, a specific component may be generated through a reaction catalyzed by the immobilized enzyme. The concentration of lactate in the microbial culture may be determined based on the concentration of the specific component. In some embodiments, a detector in the second detector assembly 295 may measure the concentration of $CO_2$ in the exhaust gas (also referred to as a "concentration of $CO_2$ in the microbial culture"). For example, the detector may be a gas analyzer using a sample of the exhaust gas at predetermined time intervals. In some embodiments, the gas analyzer may measure the concentration of $CO_2$ in the exhaust gas using an infrared sensor, a solid electrolyte sensor, a capacitance sensor, an optical fiber sensor, etc. Exemplary gas analyzers may include but are not limited to BlueInOne, Bioprofile® pHOx®, IRME-M Gas Analyzer, BIOLYT, etc. Taking a gas analyzer based on the infrared sensor as an example, the gas analyzer may include a gas chamber, an infrared source, an optical filter, and an infrared detecting unit. When the infrared passes through the sample of the exhaust gas, energy attenuation may occur at a specific wavelength range. The infrared detecting unit may detect the infrared that passes through the sample and determine the amount of energy attenuation and the specific wavelength range. The concentration of $CO_2$ may be determined based on the amount of energy attenuation at a specific wavelength range corresponding to $CO_2$. As another example, the sample may be conveyed to a mass spectrometer for detecting the concentration of $CO_2$. Other methods and detectors for measuring the concentration of lactate and the concentration of $CO_2$ in the exhaust gas of the microbial culture may also be implemented, which are within the protection scope of the present disclosure.

In some embodiments, the one or more detectors may generate signals encoding the one or more first target parameters. The processing device may obtain the signals from the one or more detectors to monitor the one or more first target fermentation parameters. The terminal device may obtain the signals from the one or more detectors and may display a diagram (e.g., a curve graph, a straight line graph) showing how the one or more first target fermentation parameters change over time. In some embodiments, the one or more first target fermentation parameters may be stored in a storage device.

In 406, the processing device may determine whether the one or more first target fermentation parameters satisfy the first set of parameter conditions. For instance, the processing device may determine a current time period of growing the microbial culture, and determine whether the one or more first target fermentation satisfy the one or more corresponding concentration ranges related to the current time period in the one or more subsets of fermentation conditions. For example, if the current time period of growing the microbial culture is 8-16 h, the processing device may compare the concentration of $CO_2$ and/or the concentration of lactate with the one or more corresponding concentration ranges related to 8-16 h of growing the microbial culture. In some embodiments, if the one or more first target fermentation parameters are higher than an upper limit of the one or more concentration ranges and/or lower than a lower limit of the one or more concentration ranges, the processing device may determine that the one or more first target fermentation parameters do not satisfy the first fermentation conditions. When the one or more first target fermentation parameters include both the concentration of $CO_2$ and the concentration of lactate, if at least one of the concentration of $CO_2$ or the concentration of lactate do not satisfy the one or more corresponding first subset of fermentation conditions, the processing device may determine that the first target fermentation conditions do not satisfy the first set of fermentation conditions. If the one or more first target fermentation parameters satisfy the first set of fermentation conditions, the process 400 may return to operation 404. If the one or more first target fermentation parameters do not satisfy the first set of fermentation conditions, the process 400 may proceed to operation 408.

In 408, one or more operations may be performed to adjust one or more first target fermentation parameters. In some embodiments, if the one or more fermentation parameters do not satisfy the set of parameter conditions, the processing device may send a prompt message to the terminal device, and/or generate one or more controlling signals to perform one or more operations to adjust the one or more parameter conditions. For example, when the concentration of lactate in the microbial culture does not satisfy the set of parameter conditions, the processing device may transmit a control signal to one or more components of the fermentation system 100 (e.g., one or more regulators 190) to adjust the rotor speed of a rotor connected to the one or more stirrers, the gas supply rate, the tank pressure of the fermentation tank, or the supply rate of supplementary nutrient materials, or to add antioxidants, biofilm inhibitors (e.g., D-amino acid), or to transfer a portion of microbial culture to another fermentation tank, or the like, or a combination thereof.

In some embodiments, when the concentration of $CO_2$ is higher than the upper limit of a corresponding concentration range related to a current time period of growing the microbial culture, and/or when the concentration of lactate is less than the lower limit of a corresponding concentration range related to a current time period of growing the microbial culture, the microbial culture is not growing at an optimal condition and actions should be taken to decrease one or both of these parameters. In some embodiments, when the concentration of $CO_2$ is less than the lower limit of a corresponding concentration range related to a current time period of growing the microbial culture, and/or when the concentration of lactate is higher than the lower limit of a corresponding concentration range related to a current time period of growing the microbial culture, the microbial culture is not growing at an optimal condition and actions should be taken to increase one or both of these parameters. For example, the rotor speed, the tank pressure, and/or the air supply rate, may be increased or decreased automatically (according to preset protocols) or manually (by an operator).

In some embodiments, the one or more operations for increasing the carbon dioxide concentration and/or decreasing lactate concentration in the microbial culture may include increasing the rotor speed, increasing the tank pressure, increasing the air supply rate, or decreasing the viscosity of the microbial culture, or the like, or a combination thereof. Exemplary methods for decreasing the viscosity of the microbial culture may include adding diluted or undiluted supplementary fermentation medium, buffer solution, water, or biofilm inhibitors that can inhibit, reduce, or remove biofilms formed by the microbes in the microbial culture, or the like, or a combination thereof.

In some embodiments, the rotor speed, the tank pressure, and/or the air supply rate may be increased or decreased by a preset changing value, respectively, to adjust the carbon dioxide and/or lactate concentrations in the microbial culture. Merely by way of example, the rotor speed may be increased from 260 rpm to 280 rpm (by 20 rpm), the tank pressure may be increased from 0.03 MPa to 0.04 MPa (by 0.01 MPa), and/or the air supply rate may be increased from 0.6 air volume/culture volume per minute (VVM) to 0.7 VVM (by 0.1 VVM). As used herein, the term "VVM" refers to air volume per culture volume per minute. In some embodiments, an operator of the fermentation production process may adjust the preset changing value via the terminal device. In some embodiments, the processing device may automatically adjust the preset changing value. For instance, when the difference between the one or more first target parameters and the first set of parameter conditions is greater than a difference threshold, the preset changing value may be increased so that the one or more first target parameters may be more quickly adjusted to normal values, and the impact on the production of $CoQ_{10}$ may be reduced. Merely by way of example, if the first set of parameter conditions include that the concentration of $CO_2$ may need to be maintained at 4-13% in the current time period, and the measured concentration of $CO_2$ is 0.5%, the difference between 4% and 0.5% is 3.5% and is greater than an exemplary difference threshold of 2%. Thus, the preset changing value may be increased. For instance, the rotor speed may be increased from 260 rpm to 300 rpm (by 40 rpm), the tank pressure may be increased from 0.03 MPa to 0.05 MPa (by 0.02 MPa), and/or the air supply rate may be increased from 0.6 VVM to 0.8 VVM (by 0.2 VVM).

In some embodiments, if the one or more first target parameters include the concentration of $CO_2$, and the concentration of $CO_2$ is less than the lower limit of the corresponding concentration range related to the current time period, the one or more operations may include adding supplementary nutrient materials to the microbial culture in a fed-batch mode, or increasing the supply rate of the supplementary nutrient materials in a continuous mode. In some embodiments, if the one or more first target parameters include the concentration of $CO_2$, and the concentration of $CO_2$ is greater than the upper limit of the corresponding concentration range related to the current time period, the one or more operations may include decreasing the supply rate of the supplementary nutrient materials in a continuous mode, or suspending the supply of the supplementary nutrient materials.

In 410, one or more adjusted first target fermentation parameters may be obtained from the one or more detectors after a first time period after the one or more operations are performed. The one or more first target fermentation parameters may gradually change over time due to a change in the metabolic activities of the microbes caused by the one or more operations. An exemplary first time period may be 5 min, 10 min, 15 min, or more, or less. In some embodiments, the processing device may continue to obtain the one or more adjusted first target fermentation parameters at predetermined time intervals and store the one or more first target fermentation parameters in a record. The record may demonstrate how the one or more adjusted first target fermentation parameters change over time after the one or more operations are performed and may be used for further analysis on the control of the one or more first target fermentation parameters. The adjusted first target fermentation parameters obtained after the first time period after the one or more operations are performed may be used to determine whether more operations are needed to further adjust the first target fermentation parameters.

In 412, the processing device may determine whether the one or more adjusted first target fermentation parameters satisfy the first set of parameter conditions. If the one or more adjusted first target fermentation parameters do not satisfy the first set of parameter conditions, the process 400 may return to operation 408. Operations 408-412 may be repeated until the one or more adjusted first target fermentation parameters satisfy the first set of parameter conditions. If the one or more adjusted first target fermentation parameters satisfy the first set of parameter conditions, the process 400 may return to operation 404. The one or more first target fermentation parameters may continue to be monitored at predetermined time intervals. Operations 404-412 may be repeated until a fermentation ending condition is satisfied. In some embodiments, during the controlled $CoQ_{10}$ fermentation production process, the rotor speed may range from 30-500 rpm. For example, the rotor speed may range from 240-340 rpm, 60-110 rpm, 50-150 rpm, etc. In some embodiments, during the controlled $CoQ_{10}$ fermentation production process, the tank pressure may range from 0.01-0.1 MPa. For instance, the tank pressure may be maintained at 0.02-0.08 MPa. In some embodiments, during the controlled $CoQ_{10}$ fermentation production process, the air supply rate may range from 0.1-1 VVM. For example, the air supply rate may range from 0.4-1 VVM, 0.2-1.0 VVM, etc. In some embodiments, the range and the preset changing value for the rotor speed, the tank pressure, and the air supply rate may be determined based on a coordinated control of the $CoQ_{10}$ fermentation production process, and factors such as the microorganism strain, the fermentation equipment (e.g., the size and shape of the fermentation tank), the fermentation conditions, the current time period of growing the microbial culture, or the like, or a combination thereof.

In 414, the growing of the microbial culture may be stopped when a fermentation ending condition is satisfied. In some embodiments, the fermentation ending condition may include that the increasing speed of the total amount of $CoQ_{10}$ is less than a preset increasing speed threshold; the color of stained microbes turns lighter; the concentration of microbes in the microbial culture is less than a preset concentration threshold; the time for growing the microbial culture reaches a predetermined time threshold; or the like, or any combination thereof. Details regarding determining whether the fermentation ending condition is satisfied may be found, for example, in the description in connection with operation 310 in FIG. 3. A $CoQ_{10}$-containing crude product may be obtained from the microbial culture by inactivating the microbes in the microbial culture and/or disrupting the cell walls to release the $CoQ_{10}$ from the dead cells. The purified $CoQ_{10}$ may be obtained from the $CoQ_{10}$-containing crude product through separation and purification.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 5:
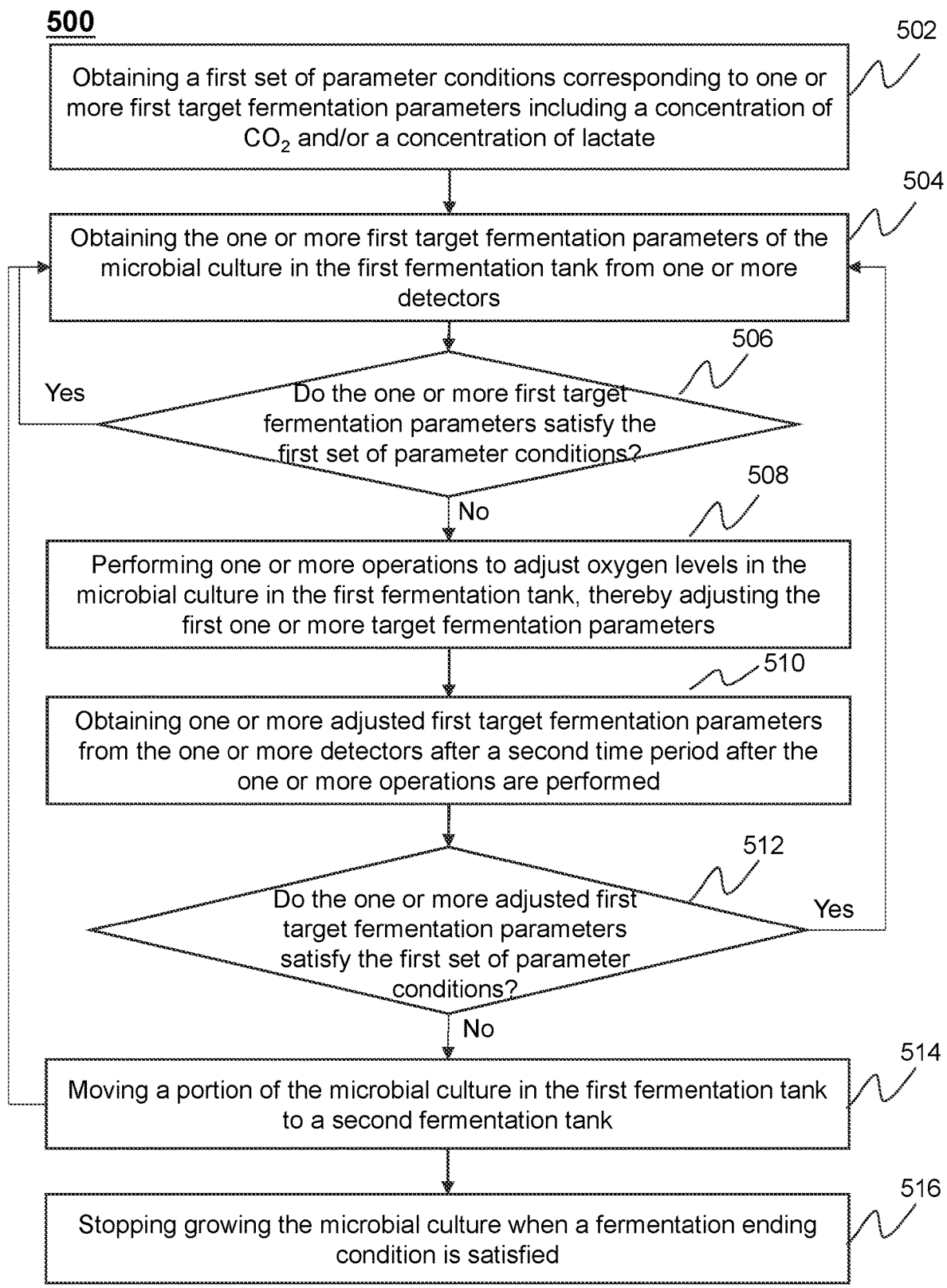
FIG. 5 is a flowchart illustrating an exemplary process for adjusting one or more first target fermentation parameters in a controlled $CoQ_{10}$ fermentation production process according to some embodiments of the present disclosure.

FIG. 5 is a flowchart of an exemplary process for adjusting one or more first target fermentation parameters in a controlled $CoQ_{10}$ fermentation production process according to some embodiments of the present disclosure. In some embodiments, the process 500 shown in FIG. 5 may be implemented in a controlled $CoQ_{10}$ fermentation production process in a fermentation tank with a volume capacity of 0.5 L-2000 m$^3$. In some embodiments, the process 500 may be implemented in a controlled $CoQ_{10}$ fermentation production process in a fermentation tank with a volume capacity of 5 L-1000 m$^3$. In some embodiments, the process 500 may be implemented in a controlled $CoQ_{10}$ fermentation production process in a fermentation tank with a volume capacity of 10 L-500 m$^3$. In some embodiments, the process 500 may be implemented in a controlled $CoQ_{10}$ fermentation production process in a fermentation tank with a volume capacity of 100 L, 160 m$^3$, 325 m$^3$, or 500 m$^3$.

In 502, a first set of parameter conditions corresponding to one or more first target fermentation parameters including a concentration of $CO_2$ and/or a concentration of lactate may be obtained.

In 504, the processing device and/or the terminal device may obtain the one or more first target fermentation parameters of the microbial culture in the first fermentation tank from one or more detectors.

In 506, the processing device may determine whether the one or more first target fermentation parameters satisfy the first set of parameter conditions.

In 508, one or more operations may be performed to adjust the one or more first target fermentation parameters in the microbial culture.

Operations 502-508 may be performed in a similar manner as operations 402-408 in FIG. 4, respectively. For brevity, a detailed description of operations 502-508 is omitted here.

In 510, one or more adjusted first target fermentation parameters may be obtained from the one or more detectors after a second time period after the one or more operations are performed. After the one or more operations are performed, the one or more first target fermentations may gradually change over time. An exemplary second time period may be 5 min, 10 min, 15 min, 30 min or the like. In some embodiments, the first time period and the second time period may be the same. In some embodiments, the second time period may be longer than the first time period. In some embodiments, the processing device may obtain the one or more adjusted first target fermentation parameters from the one or more detectors after the first time period after the one or more operations are performed. If the one or more adjusted first target fermentation parameters do not satisfy the first set of parameter conditions, the one or more operations may be performed again, as described, for example, in operations 408-412. The adjusted first target fermentation parameters obtained after the second time period after the one or more operations are performed may be used to determine whether an additional different operation is needed to further adjust the first target fermentation parameters.

In 512, the processing device may determine whether the one or more adjusted first target fermentation parameters satisfy the first set of parameter conditions. If the one or more adjusted first target fermentation parameters satisfy the first set of parameter conditions, the process 500 may return to operation 504. The monitoring of the one or more first target fermentation parameters may be continued. Operations 504-512 may be repeated until a fermentation ending condition is satisfied. In some embodiments, if the one or more adjusted first target fermentation parameters do not satisfy the first set of parameter conditions, and the microbial culture have been grown for more than a preset time period (e.g., 20 h) in the first fermentation tank, the process 500 may proceed to operation 514 to further adjust the first target fermentation parameters.

In 514, a portion of the microbial culture in the first fermentation tank may be moved to a second fermentation tank. In some embodiments, 5%-60% of the microbial culture in the first fermentation tank may be moved to the second fermentation tank. In some embodiments, 10%-50% of the microbial culture in the first fermentation tank may be moved to the second fermentation tank. In some embodiments, 25-50% of the microbial culture in the first fermentation tank may be moved to the second fermentation tank. For example, 50% of the microbial culture in the first fermentation tank may be moved to the second fermentation tank. After operation 514, the process 500 may return to operation 504. In some embodiments, the microbial culture in the first fermentation tank and the microbial culture in the second fermentation tank may be grown under appropriate conditions, respectively. The fermentation production processes in the first fermentation tank and the second fermentation tank may be controlled based on one or more fermentation parameters, respectively. Similar operations related to moving the microbial culture may be performed for one or more times.

In 516, the growing of the microbial culture may be stopped when a fermentation ending condition is satisfied. In some embodiments, the fermentation ending condition may include that an accumulation rate of the of $CoQ_{10}$ is less than a preset threshold; the color of stained microbes turns lighter; the concentration of microbes in the microbial culture is less than a preset concentration threshold; the time for growing the microbial culture reaches a predetermined time threshold; or the like, or any combination thereof. Details regarding determining whether the fermentation ending condition is satisfied may be found, for example, in the description in connection with operation 310 in FIG. 3. A $CoQ_{10}$-containing crude product may be obtained from the microbial culture by inactivating the microbes in the microbial culture and/or disrupting the cell walls to release the $CoQ_{10}$ from the dead cells. The purified $CoQ_{10}$ may be obtained from the $CoQ_{10}$-containing crude product through separation and purification.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 6:
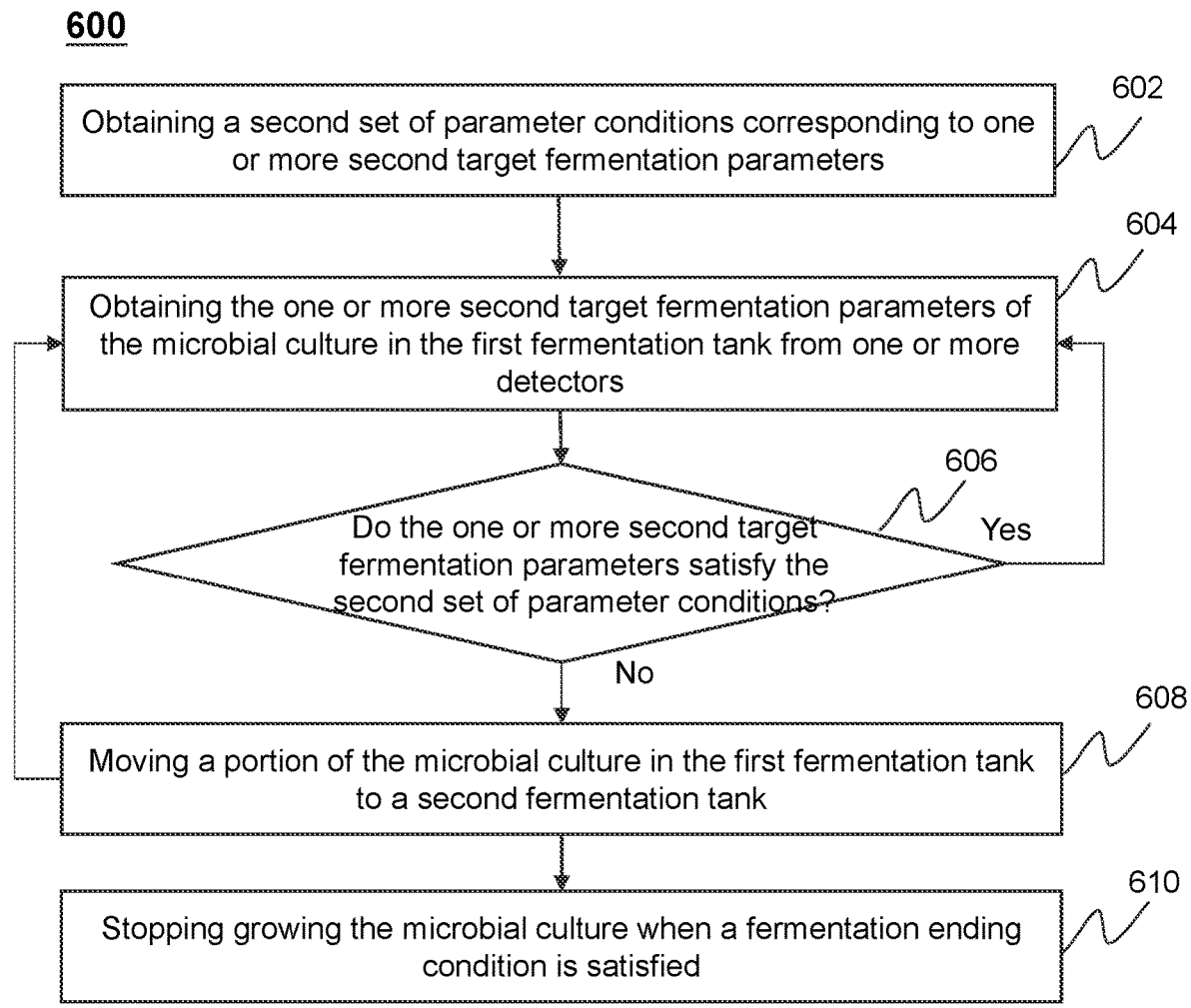
FIG. 6 is a flowchart illustrating an exemplary process for transferring a portion of the microbial culture in a first fermentation tank to a second fermentation tank based on one or more second target fermentation parameters in a controlled $CoQ_{10}$ fermentation production process according to some embodiments of the present disclosure.

FIG. 6 is a flowchart of an exemplary process for transferring a portion of the microbial culture in a first fermentation tank to a second fermentation tank based on one or more second target fermentation parameters in a controlled $CoQ_{10}$ fermentation production process according to some embodiments of the present disclosure. In some embodiments, the process 600 shown in FIG. 6 may be implemented in a controlled $CoQ_{10}$ fermentation production process in a fermentation tank with a volume capacity of 0.5 L-2000 $m^3$. In some embodiments, the process 600 may be implemented in a controlled $CoQ_{10}$ fermentation production process in a fermentation tank with a volume capacity of 5 L-1000 $m^3$. In some embodiments, the process 600 may be implemented in a controlled $CoQ_{10}$ fermentation production process in a fermentation tank with a volume capacity of 10 L-500 $m^3$. In some embodiments, the process 600 may be implemented in a controlled $CoQ_{10}$ fermentation production process in a fermentation tank with a volume capacity of 100 L, 160 $m^3$, 325 $m^3$, or 500 $m^3$.

In 602, a second set of parameter conditions corresponding to one or more second target fermentation parameters may be obtained. For instance, the second target fermentation parameters may include a concentration of $CO_2$ in the microbial culture, a concentration of lactate in the microbial culture, a conductivity of the microbial culture, or the like, or a combination thereof. The second set of parameter conditions may be stored in a storage device. The processing device may obtain the second set of parameter conditions from the storage device. In some embodiments, the second set of parameter conditions may include one or more second subsets of fermentation conditions correspond to the one or more second target fermentation parameters. Each of the one or more second subsets of fermentation conditions may include a plurality of fermentation conditions corresponding to different time periods.

In some embodiments, the second subset of fermentation conditions corresponding to the concentration of $CO_2$ in the exhaust gas of the microbial culture may include: during 0-16 h of growing the microbial culture, the concentration of $CO_2$ in the exhaust gas of the microbial culture may need to be maintained at 0.5%-15%; during 16-48 h of growing the microbial culture, the concentration of $CO_2$ in the exhaust gas of the microbial culture may need to be maintained at 2%-18%; during 48-80 h of growing the microbial culture, the concentration of $CO_2$ in the exhaust gas of the microbial culture may need to be maintained at 2%-15%; and/or after 80 h of growing the microbial culture, the concentration of $CO_2$ in the exhaust gas of the microbial culture may need to be maintained at 1%-10%.

In some embodiments, the second subset of fermentation conditions corresponding to the concentration of $CO_2$ in the exhaust gas of the microbial culture may include: during 0-16 h of growing the microbial culture, the concentration of $CO_2$ in the exhaust gas of the microbial culture may need to be maintained at 1%-10%; during 16-48 h of growing the microbial culture, the concentration of $CO_2$ in the exhaust gas of the microbial culture may need to be maintained at 5%-13%; during 48-80 h of growing the microbial culture, the concentration of $CO_2$ in the exhaust gas of the microbial culture may need to be maintained at 4%-10%; and/or after 80 h of growing the microbial culture, the concentration of $CO_2$ in the exhaust gas of the microbial culture may need to be maintained at 3%-8%.

In some embodiments, the second subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 0.5%-7%; during 8-16 h of growing the microbial culture, the concentration of $CO_2$ in the exhaust gas of the microbial culture may need to be maintained at 2%-15%; during 16-32 h of growing the microbial culture, the concentration of $CO_2$ in the exhaust gas of the microbial culture may need to be maintained at 2%-18%; during 32-48 h of growing the microbial culture, the concentration of $CO_2$ in the exhaust gas of the microbial culture may need to be maintained at 5%-15%; during 48-64 h of growing the microbial culture, the concentration of $CO_2$ in the exhaust gas of the microbial culture may need to be maintained at 4%-13%; during 64-80 h of growing the microbial culture, the concentration of $CO_2$ in the exhaust gas of the microbial culture may need to be maintained at 2%-11%; and/or after 80 h of growing the microbial culture, the concentration of $CO_2$ in the exhaust gas of the microbial culture may need to be maintained at 1%-10%.

In some embodiments, the second subset of fermentation conditions corresponding to the concentration of $CO_2$ in the exhaust gas of the microbial culture may include: during 0-8 h of growing the microbial culture, the concentration of $CO_2$ in the exhaust gas of the microbial culture may need to be maintained at 1%-5%; during 8-16 h of growing the microbial culture, the concentration of $CO_2$ in the exhaust gas of the microbial culture may need to be maintained at 3%-10%; during 16-32 h of growing the microbial culture, the concentration of $CO_2$ in the exhaust gas of the microbial culture may need to be maintained at 5%-13%; during 32-48 h of growing the microbial culture, the concentration of $CO_2$ in the exhaust gas of the microbial culture may need to be maintained at 6%-11%; during 48-64 h of growing the microbial culture, the concentration of $CO_2$ in the exhaust gas of the microbial culture may need to be maintained at 5%-10%; during 64-80 h of growing the microbial culture, the concentration of $CO_2$ in the exhaust gas of the microbial culture may need to be maintained at 4%-9%; and/or after 80 h of growing the microbial culture, the concentration of $CO_2$ in the exhaust gas of the microbial culture may need to be maintained at 3%-8%.

In some embodiments, the second subset of fermentation conditions corresponding to the concentration of lactate in the microbial culture may include: during 0-16 h of growing the microbial culture, the concentration of lactate in the microbial culture may need to be maintained at 4-80 mg/L; during 16-48 h of growing the microbial culture, the concentration of lactate in the microbial culture may need to be maintained at 8-140 mg/L; during 48-80 h of growing the microbial culture, the concentration of lactate in the microbial culture may need to be maintained at 15-200 mg/L; and/or after 80 h of growing the microbial culture, the concentration of lactate in the microbial culture may need to be maintained at 30-140 mg/L.

In some embodiments, the second subset of fermentation conditions corresponding to the concentration of lactate in the microbial culture may include: during 0-16 h of growing the microbial culture, the concentration of lactate in the microbial culture may need to be maintained at 10-50 mg/L; during 16-48 h of growing the microbial culture, the concentration of lactate in the microbial culture may need to be maintained at 20-100 mg/L; during 48-80 h of growing the microbial culture, the concentration of lactate in the microbial culture may need to be maintained at 30-150 mg/L; and/or after 80 h of growing the microbial culture, the concentration of lactate in the microbial culture may need to be maintained at 50-100 mg/L.

In some embodiments, the second subset of fermentation conditions corresponding to the concentration of lactate in the microbial culture may include: during 0-8 h of growing the microbial culture, the concentration of lactate in the microbial culture may need to be maintained at 5-50 mg/L; during 8-16 h of growing the microbial culture, the concentration of lactate in the microbial culture may need to be maintained at 8-80 mg/L; during 16-32 h of growing the microbial culture, the concentration of lactate in the microbial culture may need to be maintained at 8-70 mg/L; during 32-48 h of growing the microbial culture, the concentration of lactate in the microbial culture may need to be maintained at 20-140 mg/L; during 48-64 h of growing the microbial culture, the concentration of lactate in the microbial culture may need to be maintained at 15-200 mg/L; during 64-80 h of growing the microbial culture, the concentration of lactate in the microbial culture may need to be maintained at 40-190 mg/L; and/or after 80 h of growing the microbial culture, the concentration of lactate in the microbial culture may need to be maintained at 40-120 mg/L.

In some embodiments, the second subset of fermentation conditions corresponding to the concentration of lactate in the microbial culture may include: during 0-8 h of growing the microbial culture, the concentration of lactate in the microbial culture may need to be maintained at 10-30 mg/L; during 8-16 h of growing the microbial culture, the concentration of lactate in the microbial culture may need to be maintained at 10-50 mg/L; during 16-32 h of growing the microbial culture, the concentration of lactate in the microbial culture may need to be maintained at 20-50 mg/L; during 32-48 h of growing the microbial culture, the concentration of lactate in the microbial culture may need to be maintained at 30-100 mg/L; during 48-64 h of growing the microbial culture, the concentration of lactate in the microbial culture may need to be maintained at 30-150 mg/L; during 64-80 h of growing the microbial culture, the concentration of lactate in the microbial culture may need to be maintained at 50-150 mg/L; and/or after 80 h of growing the microbial culture, the concentration of lactate in the microbial culture may need to be maintained at 50-100 mg/L.

In 604, the processing device and/or the terminal device may obtain the one or more second target fermentation parameters of the microbial culture in the first fermentation tank from one or more detectors.

Operations 604 may be performed in a similar manner as operations 404 in FIG. 4. For brevity, a detailed description of operation 604 may be omitted here.

In 606, the processing device may determine whether the one or more second target fermentation parameters satisfy the second set of parameter conditions. For instance, the processing device may determine a current time period of growing the microbial culture, and determine whether the one or more second target fermentation parameters satisfy the one or more corresponding concentration ranges related to the current time period in the one or more subsets of fermentation conditions. In some embodiments, if the one or more second target fermentation parameters are higher than an upper limit of the one or more concentration ranges and/or lower than a lower limit of the one or more concentration ranges, the processing device may determine that the one or more second target fermentation parameters do not satisfy the second fermentation conditions. When the one or more second target fermentation parameters include both the concentration of $CO_2$ and the concentration of lactate, if at least one of the concentration of $CO_2$ or the concentration of lactate does not satisfy the one or more corresponding second subset of fermentation conditions, the processing device may determine that the second target fermentation conditions do not satisfy the second set of fermentation conditions. If the one or more second target fermentation parameters satisfy the second set of fermentation conditions, the process 600 may return to operation 606. If the one or more second target fermentation parameters do not satisfy the second set of fermentation conditions, and the microbial culture have been grown for more than a preset time period (e.g., 16 h, 20 h) in the first fermentation tank, the process 600 may proceed to operation 608.

In 608, a portion of the microbial culture in the first fermentation tank may be moved to a second fermentation tank. In some embodiments, 5%-60% of the microbial culture in the first fermentation tank may be moved to the second fermentation tank. In some embodiments, 10%-50% of the microbial culture in the first fermentation tank may be moved to the second fermentation tank. In some embodiments, 25-50% of the microbial culture in the first fermentation tank may be moved to the second fermentation tank. For example, 50% of the microbial culture in the first fermentation tank may be moved to the second fermentation tank. After operation 608, the process 600 may return to operation 602. In some embodiments, the microbial culture in the first fermentation tank and the microbial culture in the second fermentation tank may be grown under appropriate conditions, respectively. The fermentation production processes in the first fermentation tank and the second fermentation tank may be controlled based on one or more fermentation parameters, respectively. Similar operations related to moving the microbial culture may be performed for one or more times.

In 610, the growing of the microbial culture may be stopped when a fermentation ending condition is satisfied. In some embodiments, the fermentation ending condition may include that the increasing speed of the total amount of $CoQ_{10}$ is less than a preset increasing speed threshold; the color of stained microbes turns lighter; the concentration of microbes in the microbial culture is less than a preset concentration threshold; the time for growing the microbial culture reaches a predetermined time threshold; or the like, or any combination thereof. Details regarding determining whether the fermentation ending condition is satisfied may be found, for example, in the description in connection with operation 310 in FIG. 3. A $CoQ_{10}$-containing crude product may be obtained from the microbial culture by inactivating the microbes in the microbial culture and/or disrupting the cell walls to release the $CoQ_{10}$ from the dead cells. The purified $CoQ_{10}$ may be obtained from the $CoQ_{10}$-containing crude product through separation and purification.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

Figure 7:
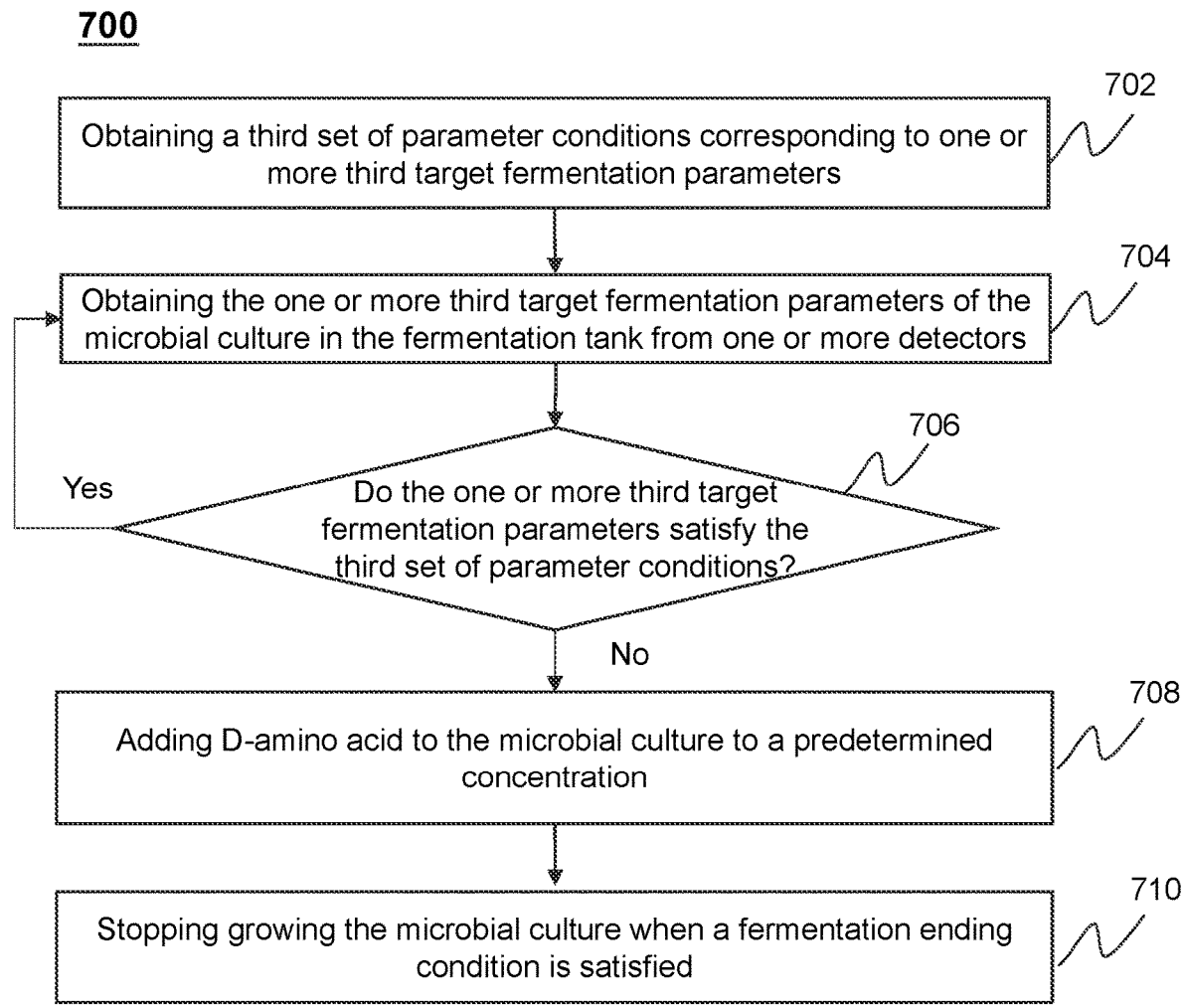
FIG. 7 is a flowchart illustrating an exemplary process for adding D-amino acid based on one or more third target fermentation parameters in a controlled $CoQ_{10}$ fermentation production process according to some embodiments of the present disclosure.

FIG. 7 is a flowchart of an exemplary process for adding D-amino acid based on one or more third target fermentation parameters in a controlled $CoQ_{10}$ fermentation production process according to some embodiments of the present disclosure. In some embodiments, the process 700 shown in FIG. 7 may be implemented in a controlled $CoQ_{10}$ fermentation production process in a fermentation tank with a volume capacity of 0.5 L-2000 m³. In some embodiments, the process 600 may be implemented in a controlled $CoQ_{10}$ fermentation production process in a fermentation tank with a volume capacity of 5 L-1000 m³. In some embodiments, the process 600 may be implemented in a controlled $CoQ_{10}$ fermentation production process in a fermentation tank with a volume capacity of 10 L-500 m³. In some embodiments, the process 600 may be implemented in a controlled $CoQ_{10}$ fermentation production process in a fermentation tank with a volume capacity of 100 L, 160 m³, 325 m³, or 500 m³.

In 702, a third set of parameter conditions corresponding to one or more third target fermentation parameters may be obtained. For instance, the third target fermentation parameters may include a concentration of $CO_2$ in the microbial culture, a concentration of lactate in the microbial culture, a conductivity of the microbial culture, or the like, or a combination thereof. The third set of parameter conditions may be stored in a storage device. The processing device may obtain the third set of parameter conditions from the storage device. In some embodiments, the third set of parameter conditions may include one or more third subsets of fermentation conditions correspond to the one or more third target fermentation parameters. Each of the one or more third subsets of fermentation conditions may include a plurality of fermentation conditions corresponding to different time periods.

In some embodiments, the third subset of parameter conditions corresponding to the concentration of $CO_2$ in the exhaust gas of the microbial culture may include that the concentration of $CO_2$ in the exhaust gas of the microbial culture may need to be less than 3%. In some embodiments, the third subset of parameter conditions corresponding to the concentration of $CO_2$ in the exhaust gas of the microbial culture may include that the concentration of $CO_2$ in the exhaust gas of the microbial culture may need to be less than 3% during 16-48 h of growing the microbial culture. In some embodiments, the third subset of parameter conditions corresponding to the concentration of $CO_2$ in the exhaust gas of the microbial culture may include that the concentration of $CO_2$ in the exhaust gas of the microbial culture may need to be less than 3% during 48 h-80 h of growing the microbial culture. In some embodiments, the third subset of parameter conditions corresponding to the concentration of $CO_2$ in the exhaust gas of the microbial culture may include that the concentration of $CO_2$ in the exhaust gas of the microbial culture may need to be less than 2% during after 80 h of growing the microbial culture.

In some embodiments, the third subset of parameter conditions corresponding to the concentration of lactate in the microbial culture may include that the concentration of lactate in the microbial culture may need to be more than 50 mg/L. In some embodiments, the third subset of parameter conditions corresponding to the concentration of lactate in the microbial culture may include that the concentration of lactate in the microbial culture may need to be more than 120 mg/L during 16-48 h of growing the microbial culture. In some embodiments, the third subset of parameter conditions corresponding to the concentration of lactate in the microbial culture may include that the concentration of lactate in the microbial culture may need to be more than 120 mg/L during 48-80 h of growing the microbial culture.

In 704, the processing device and/or the terminal device may obtain the one or more third target fermentation parameters of the microbial culture in the fermentation tank from one or more detectors. In some embodiments, operation 704 may be performed in a similar manner as operation 404. The one or more third target fermentation parameters may be used to determine whether operations are needed to prevent, reduce, or remove the biofilms in the microbial culture. Since biofilms may affect the absorption of dissolved oxygen by the microbes, the metabolism of the microbes may be converted from aerobic metabolism to anaerobic metabolism. In some embodiments, the concentration of $CO_2$ in the exhaust gas of the microbial culture may be decreased, and the concentration of lactate in the microbial culture may be increased. Thus the metabolism of the microbes may be affected.

In 706, the processing device may determine whether the one or more third target fermentation parameters satisfy the third set of parameter conditions. For instance, the processing device may determine a current time period of growing the microbial culture, and determine whether the one or more third target fermentation parameters satisfy the one or more corresponding concentration ranges related to the current time period in the one or more subsets of fermentation conditions. In some embodiments, if the one or more third target fermentation parameters are higher than an upper limit of the one or more concentration ranges, the processing device may determine that the one or more third target fermentation parameters do not satisfy the third fermentation conditions. When the one or more third target fermentation parameters include both the concentration of $CO_2$ and the concentration of lactate, if at least one of the concentration of $CO_2$ or the concentration of lactate does not satisfy the one or more corresponding third subset of fermentation conditions, the processing device may determine that the third target fermentation conditions do not satisfy the third set of fermentation conditions. If the one or more third target fermentation parameters satisfy the third set of fermentation conditions, the process 700 may return to operation 704. If the one or more third target fermentation parameters do not satisfy the third set of fermentation conditions, and the microbial culture have been grown for more than a preset time period (e.g., 20 h) in the first fermentation tank, the process 700 may proceed to operation 708.

In 708, D-amino acid may be added to the microbial culture to a predetermined concentration. As used herein, the predetermined concentration may refer to the concentration of D-amino acid in the microbial culture after the addition of D-amino acid. The D-amino acid may prevent, remove, reduce, disperse, disrupt, or eradicate biofilms in the microbial culture, and thus the transfer efficiency of materials (e.g., oxygen, carbon source) between the microbes and the fermentation medium may be improved. The D-amino acid may include but is not limited to D-tyrosine, D-aspartic acid, D-arginine, D-methionine, D-leucine, D-tryptophan, D-phenylalanine, D-asparagine, D-glutamine, D-serine, D-glycine, D-lysine, D-cysteine, D-histidine, D-valine, D-proline, D-isoleucine, D-threonine, D-glutamic acid, D-alanine, or the like, or a combination thereof, depending on the microbes used in the controlled fermentation production process. For example, in a controlled $CoQ_{10}$ fermentation production process using *Rhodobacter sphaeroides*, the D-amino acid may include one or more of D-tyrosine, D-aspartic acid, D-arginine, D-methionine, D-leucine, D-tryptophan, and D-phenylalanine. In some embodiments, the predetermined concentration may be a total concentration of one or more types of D-amino acid mentioned above. In some embodiments, the predetermined concentration may be 1 μM-5 mM. In some embodiments, the predetermined concentration may be 10 μM-2 mM. In some embodiments, the predetermined concentration may be 100 μM-1 mM. For instance, the predetermined concentration may be 500 μM, 1 mM, 1.5 mM, etc. In some embodiments, a powder form or an aqueous solution of the D-amino acid may be added to the microbial culture. In some embodiments, the D-amino acid may be added to the microbial culture through a single addition operation. In some embodiments, a required amount of D-amino acid may be added to the microbial culture though multiple times of addition.

In some embodiments, after the D-amino acid is added to the microbial culture, the process 700 may return to operation 704 to continue to monitor the third set of fermentation parameters at the predetermined time intervals. When the third set of fermentation parameters do not satisfy the third set of parameter conditions, more D-amino acid may be added to the microbial culture.

In some embodiments, apart from the D-amino acid, one or more other anti-biofilm agents may also be added to the microbial culture to obtain a synergistic effect on preventing, removing, reducing, dispersing, disrupting, or eradicating the biofilms. The anti-biofilm agents may include but are not limited to acyl homoserine lactones, autoinducer-2, Bis-(3'5')-cyclic di-guanylic acid, indole or a derivative of indole, cis decenoic acid, cis-11-methyl-2-dodecenoic acid, or the like, or a combination thereof.

In 710, the growing of the microbial culture may be stopped when a fermentation ending condition is satisfied. In some embodiments, the fermentation ending condition may include that the increasing speed of the total amount of $CoQ_{10}$ is less than a preset increasing speed threshold; the color of stained microbes turns lighter; the concentration of microbes in the microbial culture is less than a preset concentration threshold; the time for growing the microbial culture reaches a predetermined time threshold; or the like, or any combination thereof. Details regarding determining whether the fermentation ending condition is satisfied may be found, for example, in the description in connection with operation 310 in FIG. 3. A $CoQ_{10}$-containing crude product may be obtained from the microbial culture by inactivating the microbes in the microbial culture and/or disrupting the cell walls to release the $CoQ_{10}$ from the dead cells. The purified $CoQ_{10}$ may be obtained from the $CoQ_{10}$-containing crude product through separation and purification.

It should be noted that the above description is merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure.

The present disclosure is further described according to the following examples, which should not be construed as limiting the scope of the present disclosure.

EXAMPLES

Microorganism Strain

The microorganism strain used for producing $CoQ_{10}$ through the fermentation production processes in Examples 1-5 was *Rhodobacter sphaeroides* JDW-610 (referred to as "JDW-610 strain" in the following description). The JDW-610 strain was obtained from the China General Microbiological Culture Collection Center (CGMCC, NO. 1 West Beichen Road, Chaoyang District, Beijing, China, 100101). The preservation number for the JDW-610 strain was CGMCC No. 4497 and the preservation date for the JDW-610 strain was Dec. 21, 2010.

Culture Medium, Supplementary Carbon Source and Nitrogen Source

The agar slant medium used in the examples 1-5 was prepared using 10 g/L of glucose, 5 g/L of yeast extract, 5 g/L of peptone, 5 g/L of NaCl, 0.5 g/L of $(NH_4)_2SO_4$, 1 μg/L of vitamin $B_1$, 1 μg/L of vitamin K, 1.5 μg/L of vitamin A, 0.8 μg/L of $Na_2MoO_4.2H_2O$, 1.2 μg/L of $ZnSO_4.7H_2O$, 0.33 μg/L of $KNO_3$, 0.44 μg/L of NaBr, and 20 g/L of agar. The pH value of the agar slant medium was adjusted to 7.2. The agar slant medium was sterilized at 121° C. for 25 min.

The preliminary culture medium used in Examples 1-5 was prepared using solid components and liquid components. The weight ratio of bran, rice, and millet in the solid components was 25%, 25%, and 50%, respectively. The liquid components were prepared using 10 g/L of glucose, 5 g/L of yeast extract, 5 g/L of peptone, 5 g/L of NaCl, 2 g/L of $CaCl_2$), 0.5 g/L of $(NH_4)_2SO_4$, 1 μg/L of vitamin $B_1$, 1 μg/L vitamin K, 1.5 μg/L of vitamin A, 0.6 μg/L of $CuSO_4.5H_2O$, 0.8 μg/L of $Na_2MoO_4.2H_2O$, 1.2 μg/L of $ZnSO_4.7H_2O$, 0.33 μg/L $KNO_3$, and 0.44 μg/L NaBr. The pH value of the liquid components was adjusted to 7.2. The weight ratio of the solid components to the liquid components was 10:7. The solid components and the liquid components were mixed and heated at 80° C. for 40 min. The mixture was dried in the air. The dried mixture was used as the preliminary culture medium and was added to a plurality of 1000 mL K type cylinders. Each of the plurality of K type cylinders contained 200 g of the preliminary culture medium. The preliminary culture medium was sterilized at 121° C. for 30 min.

The first seed medium used in Examples 1-5 was prepared using 15 g/L of glucose, 7 g/L of yeast extract, 6.5 g/L of peptone, 6.5 g/L of NaCl, 5 g/L of $CaCO_3$, 0.6 μg/L of $CuSO_4.5H_2O$, 0.8 μg/L of $Na_2MoO_4.2H_2O$, 1.2 μg/L of $ZnSO_4.7H_2O$, 0.33 μg/L of $KNO_3$, 0.44 μg/L of NaBr. The pH value of the first seed medium was adjusted to 5.8. The first seed medium was sterilized at 121° C. for 30 min.

The fermentation medium used in Examples 1-5 included 20 g/L of glucose, 10 g/L of yeast extract, 10 g/L of peptone, 10 g/L of NaCl, 40 g/L of corn steep power, 5 g/L of $(NH_4)_2SO_4$, 5 g/L of $CaCO_3$, 1.2 μg/L of $CuSO_4.5H_2O$, 1.6 μg/L of $Na_2MoO_4.2H_2O$, 2.4 μg/L of $ZnSO_4.7H_2O$, 0.66 μg/L of $KNO_3$, 0.88 μg/L of NaBr. The pH value of the fermentation medium was adjusted to 5.8. The fermentation medium was sterilized at 121° C. for 30 min.

The supplementary carbon source used in Examples 1-5 was a 40% glucose solution. The glucose solution was sterilized at 118° C. for 25 min.

The supplementary nitrogen source used in Examples 1-5 was a 28% aqueous solution of ammonia. The aqueous solution of ammonia was also used to adjust the pH of the microbial culture.

Preparation of the Target Microbial Suspension

Samples of the JDW-610 strain obtained from the CGMCC were inoculated on the agar slant medium and cultured at 30° C. in the dark for 24 h. The JDW-610 strain grown on the agar slant medium was preserved at 4° C. Before a fermentation production process, the preserved JDW-610 strain was re-inoculated on fresh agar slant medium to obtain a resuscitated JDW-610 strain. The bacteria were suspended in sterilized water to obtain a bacterial suspension. The bacterial suspension was added to the preliminary culture medium and mixed. The mixture was cultured at 30° C. in the dark for 12 h and then remixed. The resultant was cultured at 30° C. in the dark for another 12 h to obtain a first microbial culture. Samples of the first microbial culture were added to 400 mL of sterilized water, and at least a part of the bacterial lawn on the surface of the solid components in the preliminary culture medium was washed off. The resultant was filtered to obtain the first target bacterial suspension. More details for preparing the target bacterial suspension may be found in, for example, Chinese Patent No. 102154182B, entitled "Fermentation culture method of solid material mother strain produced from coenzyme $Q_{10}$", filed on Mar. 2, 2011, the contents of which are hereby incorporated by reference.

Example 1

Control of a Fermentation Production Process in a 100 L Fermentation Tank

A fermentation production process for producing $CoQ_{10}$ using the JDW-610 strain was carried out in a fermentation tank having the volume of 100 L. The first target bacterial suspension was inoculated in the first seed medium in a seed tank of 30 L, and a volume ratio of the inoculated target bacterial suspension to the first seed medium was 1.2%. The resultant volume was 15 L. The mixture was cultured at 30° C. in the dark under pH 5.5-8.5 at a rotor speed of 200 rpm for 30 h to obtain a first seed culture. The first seed culture was used as the target seed culture. During the culturing process of the first seed culture, the pressure of the seed tank was maintained at 0.02-0.04 MPa and the air supply rate was maintained at 0.8-1.1 $m^3/h$. The first seed culture was further inoculated in the fermentation medium in a fermentation tank of 100 L to obtain the microbial culture and start the fermentation production process. The volume ratio of the inoculated first seed culture to the fermentation medium was 10% and the volume of the microbial culture after inoculation was 45-55 L. The microbial culture was grown at 32° C. under pH 5.5-8.5. During the fermentation production process, the rotor speed was maintained at 240-340 rpm, the tank pressure was maintained at 0.02-0.08 MPa, and the air supply rate was maintained at 0.4-1 VVM. Supplementary carbon source, supplementary nitrogen source, and supplementary phosphorus were provided to the microbial culture during growing the microbial culture to maintain the concentration of saccharide (e.g., reducing sugar) at 1 to 15 g/L, the pH at 5.5-8.5, and the concentration of phosphorus at 0.05 to 0.8 g/L.

The concentration of $CO_2$ in the exhaust gas of the microbial culture was measured using a mass spectrometer. During 0-8 h of growing the microbial culture, the concentration of $CO_2$ in the exhaust gas of the microbial culture was maintained at 1%-4%. During 8-16 h of growing the microbial culture, the concentration of $CO_2$ in the exhaust gas of the microbial culture was maintained at 4%-8%. During 16-36 h of growing the microbial culture, the concentration of $CO_2$ in the exhaust gas of the microbial culture was maintained at 7%-12%. During 36-48 h of growing the microbial culture, the concentration of $CO_2$ in the exhaust gas of the microbial culture was maintained at 6%-10%. During 48-68 h of growing the microbial culture, the concentration of $CO_2$ in the exhaust gas of the microbial culture was maintained at 5%-8%. During 68-80 h of growing the microbial culture, the concentration of $CO_2$ in the exhaust gas of the microbial culture was maintained at 5%-9%. During 80-100 h of growing the microbial culture, the concentration of $CO_2$ in the exhaust gas of the microbial culture was maintained at 4%-7%.

When the concentration of $CO_2$ in the exhaust gas of the microbial culture was higher than the upper limit of a corresponding concentration range related to a current time period of growing the microbial culture, the rotor speed, the tank pressure, or the air supply rate, or a combination thereof was decreased. When the concentration of $CO_2$ in the exhaust gas of the microbial culture was lower than the lower limit of the corresponding concentration range related to the time period, the rotor speed, the tank pressure, or the air supply rate, or a combination thereof was increased. When the concentration of $CO_2$ in the exhaust gas of the microbial culture could not be maintained at the predetermined concentration range by adjusting the rotor speed, the tank pressure, or the air supply rate, 10%-40% of the microbial culture in the fermentation tank was transferred to another fermentation tank and grown separately. Then the concentration of $CO_2$ in the exhaust gas of the microbial culture of the fermentation tanks was maintained similarly in predetermined ranges.

When the concentration of $CO_2$ in the exhaust gas of the microbial culture was less than 3% during 16-80 h of growing the microbial culture or less than 2% after 80 h of growing the microbial culture, D-amino acid was added to the microbial culture to reach the concentration of 2 mM, so as to inhibit the formation of biofilm and improve the transfer efficiency of materials between the bacteria and the fermentation medium. A mixture including various D-amino acids was added into the microbial culture. The D-amino acids included D-tyrosine, D-aspartic acid, D-arginine, and D-methionine. Specifically, the D-amino acids included 50% D-tyrosine by weight, 15% D-aspartic acid by weight, 20% D-arginine by weight, and 15% D-methionine by weight.

After 100 h of growing the microbial culture, the concentration of $CoQ_{10}$ in the microbial culture was measured using HPLC. The Hypersil™ ODS chromatographic column made of stainless steel was used to measure the concentration of $CoQ_{10}$, which had a diameter of 4.6 mM, a height of 150 mM, and a particle size of 5 μm. The wave length for measuring the concentration of $CoQ_{10}$ was 275 nm. The mobile phase included 35% absolute ethanol and 65% absolute methanol. The flow rate was controlled to maintain the retention time of the $CoQ_{10}$ at about 11 min. In some embodiments, the flow rate was 1.1 mL/min. The temperature for the measurement was maintained at 35° C. The concentration of $CoQ_{10}$ in the microbial culture was about 3460 mg/L.

Example 2

Control of a Fermentation Production Process in a 160 m³ Fermentation Tank

A fermentation production process for producing $CoQ_{10}$ using the JDW-610 strain was carried out in a fermentation tank having the volume of 160 m³. The volume of the microbial culture after inoculation was 70-90 m³. The microbial culture was grown at 32° C. under pH 5.5-8.5. During the fermentation production process, the rotor speed was maintained at 60-110 rpm, the tank pressure was maintained at 0.02-0.08 MPa, and the air supply rate was maintained at 0.2-1.0 VVM. Supplementary carbon source, supplementary nitrogen source, and supplementary phosphorus were provided to the microbial culture during growing the microbial culture to maintain the concentration of saccharide (e.g., reducing sugar) at 1 to 15 g/L, the pH at 5.5-8.5, and the concentration of phosphorus at 0.05 to 0.8 g/L.

The concentration of $CO_2$ in the exhaust gas of the microbial culture was measured using the mass spectrometer mentioned in Example 1. During 0-8 h of growing the microbial culture, the concentration of $CO_2$ in the exhaust gas of the microbial culture was maintained at 2%-4%. During 8-16 h of growing the microbial culture, the concentration of $CO_2$ in the exhaust gas of the microbial culture was maintained at 3%-9%. During 16-36 h of growing the microbial culture, the concentration of $CO_2$ in the exhaust gas of the microbial culture was maintained at 6%-11%. During 36-48 h of growing the microbial culture, the concentration of $CO_2$ in the exhaust gas of the microbial culture was maintained at 7%-10%. During 48-68 h of growing the microbial culture, the concentration of $CO_2$ in the exhaust gas of the microbial culture was maintained at 6%-9%. During 68-80 h of growing the microbial culture, the concentration of $CO_2$ in the exhaust gas of the microbial culture was maintained at 4%-8%. During 80-100 h of growing the microbial culture, the concentration of $CO_2$ in the exhaust gas of the microbial culture was maintained at 3%-7%.

When the concentration of $CO_2$ in the exhaust gas of the microbial culture was not within the predetermined concentration range, at least one of the rotor speed, the tank pressure, or the air supply rate was adjusted, or 30-50% of the microbial culture was transferred to an empty fermentation tank, in a similar manner as described in Example 1.

When the concentration of $CO_2$ in the exhaust gas of the microbial culture was less than 3% during 16-80 h of growing the microbial culture or less than 2% after 80 h of growing the microbial culture, D-amino acid was added to the microbial culture to reach the concentration of 1 mM, so as to inhibit the formation of biofilm and improve the transfer efficiency of materials between the bacteria and the fermentation medium. The D-amino acid included D-tyrosine, D-aspartic acid, D-arginine, and D-methionine. In some embodiments, a mixture including different D-amino acids was added into the microbial culture. The mixture included 40% D-tyrosine by weight, 15% D-aspartic acid by weight, 30% D-arginine by weight, and 15% D-methionine by weight.

After 100 h of growing the microbial culture, the concentration of $CoQ_{10}$ in the microbial culture was about 3550 mg/L. The concentration of $CoQ_{10}$ in the microbial culture was measured using HPLC as described in Example 1.

Example 3

Control of a Fermentation Production Process in a 325 m³ Fermentation Tank

A fermentation production process for producing $CoQ_{10}$ using the JDW-610 strain was carried out in a fermentation tank having the volume of 325 m³. The volume of the microbial culture after inoculation was 150 to 190 m³. The microbial culture was grown at 32° C. under pH 5.5-8.5. During the fermentation production process, the rotor speed was maintained at 50-150 rpm, the tank pressure was maintained at 0.02-0.08 MPa, and the air supply rate was maintained at 0.2-1.0 VVM. Supplementary carbon source, supplementary nitrogen source, and supplementary phosphorus were provided to the microbial culture during growing the microbial culture to maintain the concentration of saccharide (e.g., reducing sugar) at 1 to 15 g/L, the pH at 5.5-8.5, and the concentration of phosphorus at 0.05 to 0.8 g/L.

The concentration of $CO_2$ in the exhaust gas of the microbial culture was measured using the mass spectrometer mentioned in Example 1. During 0-8 h of growing the microbial culture, the concentration of $CO_2$ in the exhaust gas of the microbial culture was maintained at 1%-5%. During 8-16 h of growing the microbial culture, the concentration of $CO_2$ in the exhaust gas of the microbial culture was maintained at 5%-8%. During 16-36 h of growing the microbial culture, the concentration of $CO_2$ in the exhaust gas of the microbial culture was maintained at 5%-10%. During 36-48 h of growing the microbial culture, the concentration of $CO_2$ in the exhaust gas of the microbial culture was maintained at 7%-11%. During 48-68 h of growing the microbial culture, the concentration of $CO_2$ in the exhaust gas of the microbial culture was maintained at 5%-10%. During 68-80 h of growing the microbial culture, the concentration of $CO_2$ in the exhaust gas of the microbial culture was maintained at 4%-9%. During 80-100 h of growing the microbial culture, the concentration of $CO_2$ in the exhaust gas of the microbial culture was maintained at 3%-6%.

When the concentration of $CO_2$ in the exhaust gas of the microbial culture was not within the predetermined concentration range, at least one of the rotor speed, the tank pressure, or the air supply rate was adjusted or 20-50% of the microbial culture was transferred to an empty fermentation tank, in a similar manner as described in Example 1.

When the concentration of $CO_2$ in the exhaust gas of the microbial culture is less than 3% during 16-80 h of growing the microbial culture or less than 2% after 80 h of growing the microbial culture, D-amino acid was added to the microbial culture to reach the concentration of 2 mM, so as to inhibit the formation of biofilm and improve the transfer efficiency of materials between the bacteria and the fermentation medium. The D-amino acid included D-tyrosine, D-aspartic acid, D-arginine, and D-methionine. In some embodiments, a mixture including different D-amino acids was added into the microbial culture. The mixture included 45% D-tyrosine by weight, 10% D-aspartic acid by weight, 30% D-arginine by weight, and 15% D-methionine by weight.

After 100 h of growing the microbial culture, the concentration of $CoQ_{10}$ in the microbial culture was about 3540 mg/L. The concentration of $CoQ_{10}$ in the microbial culture was measured using HPLC as described in Example 1.

Example 4

Control of a Fermentation Production Process in a 160 m³ Fermentation Tank

A fermentation production process for producing $CoQ_{10}$ using the JDW-610 strain was carried out in a fermentation tank having the volume of 160 m³. The volume of the microbial culture after inoculation was 70 to 90 m³. The microbial culture was grown at 32° C. under pH 5.5-8.5. During the fermentation production process, the rotor speed was maintained at 60-110 rpm, the tank pressure was maintained at 0.02-0.08 MPa, and the air supply rate was maintained at 0.2-1.0 VVM. Supplementary carbon source, supplementary nitrogen source, and supplementary phosphorus were provided to the microbial culture during growing the microbial culture to maintain the concentration of saccharide (e.g., reducing sugar) at 1 to 15 g/L, the pH at 5.5-8.5, and the concentration of phosphorus at 0.05 to 0.8 g/L.

The concentration of lactate in the microbial culture was measured using SBA-60 Online Analysis and Control System (Institute of Biology, Shandong Academy of Sciences, China). During 0-12 h of growing the microbial culture, the concentration of lactate in the microbial culture was maintained at 10-30 mg/L. During 12-24 h of growing the microbial culture, the concentration of lactate in the microbial culture was maintained at 20-50 mg/L. During 24-40 h of growing the microbial culture, the concentration of lactate in the microbial culture was maintained at 20-100 mg/L. During 40-52 h of growing the microbial culture, the concentration of lactate in the microbial culture was maintained at 50-150 mg/L. During 48-68 h of growing the microbial culture, the concentration of lactate in the microbial culture was maintained at 50-80 mg/L. During 52-80 h of growing the microbial culture, the concentration of lactate in the microbial culture was maintained at 60-130 mg/L. During 80-100 h of growing the microbial culture, the concentration of lactate in the microbial culture was maintained at 50-100 mg/L.

When the concentration of lactate in the microbial culture was higher than the upper limit of a corresponding concentration range related to a current time period of growing the microbial culture, the rotor speed, the tank pressure, or the air supply rate, or a combination thereof was increased. When the concentration of lactate in the microbial culture was lower than the lower limit of the predetermined concentration range corresponding, the rotor speed, the tank pressure, or the air supply rate, or a combination thereof was decreased. When the concentration of lactate in the microbial culture could not be maintained at the predetermined concentration range by adjusting at least one of the rotor speed, the tank pressure, or the air supply rate, 20%-40% of the microbial culture in the fermentation tank was moved to an empty fermentation tank and grown separately. Then the lactate concentration in the microbial medium was monitored and controlled.

When the concentration of lactate in the microbial culture was higher than 70 mg/L, D-amino acid was added to the microbial culture to reach the concentration of 1 mM so as to inhibit the formation of biofilm and improve the transfer efficiency of materials between the bacteria and the fermentation medium. The D-amino acid included D-tyrosine, D-aspartic acid, D-arginine, and D-methionine. In some embodiments, a mixture including different D-amino acids was added into the microbial culture. The mixture included 35% D-tyrosine by weight, 20% D-aspartic acid by weight, 30% D-arginine by weight, and 15% D-methionine by weight.

After 100 h of growing the microbial culture, the concentration of $CoQ_{10}$ in the microbial culture was about 3570 mg/L. The concentration of $CoQ_{10}$ in the microbial culture was measured using HPLC as described in Example 1.

Example 5

Control of a Fermentation Production Process in a 325 m³ Fermentation Tank

A fermentation production process for producing $CoQ_{10}$ using the JDW-610 strain was carried out in a fermentation tank having the volume of 325 m³. The volume of the microbial culture after inoculation was 100-150 m³. The microbial culture was grown at 32° C. under pH 5.5-8.5. During the fermentation production process, the rotor speed was maintained at 50-150 rpm, the tank pressure was maintained at 0.02-0.08 MPa, and the air supply rate was maintained at 0.3-0.9 VVM. Supplementary carbon source, supplementary nitrogen source, and supplementary phosphorus were provided to the microbial culture during growing the microbial culture to maintain the concentration of saccharide (e.g., reducing sugar) at 1 to 15 g/L, the pH at 5.5-8.5, and the concentration of phosphorus at 0.05 to 0.8 g/L.

The concentration of lactate in the microbial culture was measured using the online measurement device mentioned in Example 4. During 0-12 h of growing the microbial culture, the concentration of lactate in the microbial culture was maintained at 10-40 mg/L. During 12-24 h of growing the microbial culture, the concentration of lactate in the microbial culture was maintained at 20-40 mg/L. During 24-40 h of growing the microbial culture, the concentration of lactate in the microbial culture was maintained at 30-90 mg/L. During 40-52 h of growing the microbial culture, the concentration of lactate in the microbial culture was maintained at 30-130 mg/L. During 48-68 h of growing the microbial culture, the concentration of lactate in the microbial culture was maintained at 50 mg/L-80 mg/L. During 52-80 h of growing the microbial culture, the concentration of lactate in the microbial culture was maintained at 50-120 mg/L. During 80-100 h of growing the microbial culture, the concentration of lactate in the microbial culture was maintained at 60-90 mg/L.

When the concentration of lactate in the microbial culture was not within the predetermined concentration range, the rotor speed, the tank pressure, or the air supply rate, or a combination thereof was adjusted. When the concentration of lactate in the microbial culture could not be maintained at the predetermined concentration range by adjusting at least one of the rotor speed, the tank pressure, or the air supply rate, 30-50% of the microbial culture was transferred to an empty fermentation tank and grown separately, in a similar manner as described in Example 4.

When the concentration of lactate in the microbial culture is higher than 100 mg/L, D-amino acid was added to the microbial culture to reach 0.3 mM so as to inhibit the formation of biofilm and improve the transfer efficiency of materials between the bacteria and the fermentation medium. The D-amino acid included D-tyrosine, D-aspartic acid, D-arginine, and D-methionine. In some embodiments, a mixture including different D-amino acids was added into the microbial culture. The mixture included 30% D-tyrosine by weight, 25% D-aspartic acid by weight, 30% D-arginine by weight, and 15% D-methionine by weight.

After 100 h of growing the microbial culture, the concentration of $CoQ_{10}$ in the microbial culture was about 3590 mg/L. The concentration of $CoQ_{10}$ in the microbial culture was measured using HPLC as described in Example 1.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer-readable medium having computer readable program code embodied thereon.

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

We claim:

1. A coenzyme $Q_{10}$ fermentation production process, comprising:
   growing a microbial culture of bacteria in a first tank by providing a carbon source and an oxygen source;
   monitoring a first fermentation parameter of the microbial culture in the first tank, the first fermentation parameter including at least one of a concentration of carbon dioxide in an exhaust gas of the microbial culture or a concentration of lactate in the microbial culture;
   determining whether the first fermentation parameter of the microbial culture in the first tank satisfies a first condition;
   in response to a determination that the first fermentation parameter does not satisfy the first condition,
   adjusting the first fermentation parameter by performing one or more operations, the one or more operations including increasing or decreasing a rotor speed, a tank pressure, or an air supply rate.

2. The process of claim 1, further comprising:
   determining whether the adjusted first fermentation parameter of the microbial culture in the first tank satisfies the first condition; and
   in response to a determination that the adjusted first fermentation parameter of the microbial culture in the first tank does not satisfy the first condition, adjusting the adjusted first fermentation parameter by performing the one or more operations.

3. The process of claim 1, further comprising:
   determining whether the adjusted first fermentation parameter of the microbial culture in the first tank satisfies the first condition; and
   in response to a determination that the adjusted first fermentation parameter of the microbial culture in the first tank does not satisfy the first condition, moving a portion of the microbial culture in the first tank into a second tank; and continuing to grow the microbial cultures in both the first tank and the second tank.

4. The process of claim 3, further comprising:
   after the portion of the microbial culture is moved, determining whether a first fermentation parameter of the microbial culture in the first tank satisfies a second condition;
   in response to a determination that the first fermentation parameter satisfies the second condition, adding D-amino acid to the microbial culture in the first tank to a predetermined concentration, wherein the second condition includes a concentration of carbon dioxide in the exhaust gas of the microbial culture is less than 3% or a concentration of lactate in the microbial culture is more than 50 mg/L.

5. The process of claim 4, wherein the D-amino acid includes one or more of D-tyrosine, D-aspartic acid, D-arginine, D-methionine, D-leucine, D-tryptophan, and D-phenylalanine.

6. The process of claim 4, wherein the predetermined concentration of the D-amino acid is 1 µM-5 mM.

7. The process of claim 4, wherein
   the second condition includes that the concentration of carbon dioxide is less than 3% during 16-48 h of growing the microbial culture.

8. The process of claim 4, wherein
the second condition includes that the concentration of carbon dioxide is less than 3% during 48-80 h of growing the microbial culture.

9. The process of claim 4, wherein
the second condition includes that the concentration of carbon dioxide is less than 2% after 80 h of growing the microbial culture.

10. The process of claim 4, wherein
the second condition includes that the concentration of lactate in the microbial culture is more than 120 mg/L during 16-48 h of growing the microbial culture.

11. The process of claim 4, wherein
the second condition includes that the concentration of lactate in the microbial culture is more than 180 mg/L during 48-80 h of growing the microbial culture.

12. The process of claim 4, wherein
the second condition includes that the concentration of lactate in the microbial culture is more than 120 mg/L after 80 h of growing the microbial culture.

13. The process of claim 4, wherein the D-amino acid is in the form of a mixture, including D-tyrosine, D-aspartic acid, D-arginine, and D-methionine.

14. The process of claim 4, wherein the mixture includes 30-50% D-tyrosine by weight, 10-20% D-aspartic acid by weight, about 30% D-arginine by weight, and about 15% D-methionine by weight.

15. The process of claim 1, wherein the first condition includes:
(1) during 0-16 h of growing the microbial culture, the concentration of carbon dioxide is maintained at 0.5%-13% or the concentration of lactate is maintained at 5-75 mg/L;
(2) during 16-48 h of growing the microbial culture, the concentration of carbon dioxide is maintained at 5%-13% or the concentration of lactate is maintained at 10-120 mg/L;
(3) during 48-80 h of growing the microbial culture, the concentration of carbon dioxide is maintained at 4%-10% or the concentration of lactate is maintained at 20-180 mg/L; and
(4) after 80 h of growing the microbial culture, the concentration of carbon dioxide is maintained at 3%-8% or the concentration of lactate is maintained at 40-120 mg/L.

16. The process of claim 1, wherein the first condition includes:
(1) during 0-16 h of growing the microbial culture, the concentration of carbon dioxide is maintained at 1%-10% or the concentration of lactate is maintained at 10-50 mg/L;
(2) during 16-48 h of growing the microbial culture, the concentration of carbon dioxide is maintained at 5%-13% or the concentration of lactate is maintained at 20-100 mg/L;
(3) during 48-80 h of growing the microbial culture, the concentration of carbon dioxide is maintained at 4%-10% or the concentration of lactate is maintained at 30-150 mg/L; and
(4) after 80 h of growing the microbial culture, the concentration of carbon dioxide is maintained at 3%-8% or the concentration of lactate is maintained at 50-100 mg/L.

17. The process of claim 1, wherein the first condition includes:
(1) during 0-8 h of growing the microbial culture, the concentration of carbon dioxide is maintained at 1%-5% or the concentration of lactate is maintained at 10-30 mg/L;
(2) during 8-16 h of growing the microbial culture, the concentration of carbon dioxide is maintained at 3%-10% or the concentration of lactate is maintained at 10-50 mg/L;
(3) during 16-32 h of growing the microbial culture, the concentration of carbon dioxide is maintained at 5%-13% or the concentration of lactate is maintained at 20-50 mg/L;
(4) during 32-48 h of growing the microbial culture, the concentration of carbon dioxide is maintained at 6%-11% or the concentration of lactate is maintained at 30-100 mg/L;
(5) during 48-64 h of growing the microbial culture, the concentration of carbon dioxide is maintained at 5%-10% or the concentration of lactate is maintained at 30-150 mg/L;
(6) during 64-80 h of growing the microbial culture, the concentration of carbon dioxide is maintained at 4%-9% or the concentration of lactate is maintained at 50-150 mg/L; and
(7) after 80 h of growing the microbial culture, the concentration of carbon dioxide is further maintained at 3%-8% or the concentration of lactate is maintained at 50-100 mg/L.

18. The process of claim 1, further comprising:
determining whether the adjusted first fermentation parameter of the microbial culture in the first tank satisfies a second condition;
in response to a determination that the adjusted first fermentation parameter satisfies the second condition, adding D-amino acid to the microbial culture to a predetermined concentration, wherein the second condition includes a concentration of carbon dioxide in the exhaust gas of the microbial culture is less than 3% or a concentration of lactate in the microbial culture is more than 50 mg/L.

19. A coenzyme $Q_{10}$ fermentation production process, comprising
growing a microbial culture of bacteria in a first tank by providing a carbon source and an oxygen source;
monitoring a first fermentation parameter of the microbial culture in the first tank, the first fermentation parameter including at least one of a concentration of carbon dioxide in an exhaust gas of the microbial culture or a concentration of lactate in the microbial culture;
determining whether the first fermentation parameter of the microbial culture in the first tank satisfies a first condition;
in response to a determination that the first fermentation parameter does not satisfy the first condition, adjusting the first fermentation parameter by performing one or more operations, the one or more operations including increasing or decreasing a rotor speed, a tank pressure, or an air supply rate;
determining whether the adjusted first fermentation parameter of the microbial culture in the first tank satisfies a second condition;
in response to a determination that the adjusted first fermentation parameter satisfies the second condition, adding D-amino acid to the microbial culture to a predetermined concentration, wherein the second condition a concentration of carbon dioxide in the exhaust gas of the microbial culture is less than 3% or a concentration of lactate in the microbial culture is more than 50 mg/L.

20. A coenzyme $Q_{10}$ fermentation production process, comprising growing a microbial culture of bacteria in a first tank by providing a carbon source and an oxygen source;

monitoring a first fermentation parameter of the microbial culture in the first tank, the first fermentation parameter including at least one of a concentration of carbon dioxide in an exhaust gas of the microbial culture or a concentration of lactate in the microbial culture;

determining whether the first fermentation parameter of the microbial culture in the first tank satisfies a first condition;

in response to a determination that the first fermentation parameter does not satisfy the first condition, adjusting the first fermentation parameter by performing one or more operations, the one or more operations including increasing or decreasing a rotor speed, a tank pressure, or an air supply rate;

determining whether the adjusted first fermentation parameter of the microbial culture in the first tank satisfies the first condition; and in response to a determination that the adjusted first fermentation parameter of the microbial culture in the first tank does not satisfy the first condition, moving a portion of the microbial culture in the first tank into a second tank; and continuing to grow the microbial cultures in both the first tank and the second tank;

after the portion of the microbial culture is moved, determining whether a first fermentation parameter of the microbial culture in the first tank satisfies a second condition;

in response to a determination that the first fermentation parameter satisfies the second condition, adding D-amino acid to the microbial culture in the first tank to a predetermined concentration.

* * * * *